United States Patent
Scott et al.

(10) Patent No.: US 8,454,934 B2
(45) Date of Patent: Jun. 4, 2013

(54) HIGH MOLECULAR WEIGHT CHELATION STRUCTURE

(75) Inventors: Mark D. Scott, Surrey (CA); Jayachandran N. Kizhakkedathu, Vancouver (CA)

(73) Assignee: Canadian Blood Services (CA)

( * ) Notice: Subject to any disclaimer, the term of this patent is extended or adjusted under 35 U.S.C. 154(b) by 2064 days.

(21) Appl. No.: 11/441,359

(22) Filed: May 25, 2006

(65) Prior Publication Data
US 2007/0274945 A1 Nov. 29, 2007

(51) Int. Cl.
*A61K 51/00* (2006.01)
*A61M 36/14* (2006.01)

(52) U.S. Cl.
USPC ........................................ 424/1.11; 424/1.69

(58) Field of Classification Search
USPC ....................................................... 424/1.69
See application file for complete search history.

(56) References Cited

U.S. PATENT DOCUMENTS

| | | | | |
|---|---|---|---|---|
| 4,863,964 A * | 9/1989 | Hedlund et al. | ............... | 514/575 |
| 5,077,389 A | 12/1991 | Takahashi et al. | | |
| 5,185,368 A | 2/1993 | Peter et al. | | |
| 6,251,278 B1 * | 6/2001 | Hammen | ...................... | 210/635 |
| 6,982,324 B1 | 1/2006 | Lu et al. | | |
| 7,038,078 B2 * | 5/2006 | Aldrich et al. | ................. | 562/512 |
| 2010/0310460 A1 * | 12/2010 | Liu et al. | ........................ | 424/9.1 |

FOREIGN PATENT DOCUMENTS

| | | | | |
|---|---|---|---|---|
| JP | 02053803 A | * | 2/1990 | |
| WO | WO0036422 | * | 6/2000 | |

OTHER PUBLICATIONS

Koh et al. (Phys. Chem. Chem. Phys. 2003, 5, 2417-2423).*
Shahalom et al. (Langmuir 2006, 22, 8311-8317).*
Alava et al. (J. Colloid Interface Sci., 2006, 293, 93-100).*
Ehleben et al. (Kidney International 1997, 51, 483-491).*
Dunn et al. (Pharm. Res. 1994, 11, 1016-1022).*
Williams et al. (Br. Med. J. 1985, 291, 448).*
Dixon et al. (Ann. Rheum. Dis. 1975, 34, 416-421).*
Hensley et al. (Macromolecules 1994, 27, 2351-2353).*
Neu et al. (J. Gene Med. 2005, 7, 992-1009).*
Hallaway, et al.; Modulation of deferoxamine tosicity and clearance by covalent attachment to biocompatible polymers; Proc. Natl. Acad. Sci. USA; vol. 86; Dec. 1989; Medical Sciences; pp. 10108-10112.
Scott, Mark D.; Intraerythrocytic Iron Chelation: A New Therapy for Thalassemia?; Hematology 2001; vol. 00; pp. 1-17.
Liu, et al.; Synthesis, Physicochemical Characterization, and Biological Evaluation of 2-(1'-Hydroxyalkyl)-3-hydroxypyridin-4-ones: Novel Iron Chelators with Enhanced $pFe^{3+}$ Values; J. Med. Chem. 1999, 42; 1999 American Chemical Society; pp. 4814-4823.
Merkofer, et al.; Redox Properties of the Iron Complexes of Orally Active Iron Chelators *CP20, CP502, CP509, and ICL670*; Helvetica Chimica Acta AG, Zurich; vol. 87; 2004; pp. 3021-3034.
Heinz, et al.; 4-[3,5-Bis(2-hydroxyphenyl)-1,2,4-triazol-1-yl]-benzoic Acid: A Novel Efficient and Selective Iron (III) Complexing Agent; Angew. Chem. Int. Ed. 1999; 38; No. 17; pp. 2568-2570.
Samuni, et al.; Multifunctional Antioxidant Activity of HBED Iron Chelator; Free Radical Biology & Medicine, vol. 30, No. 2; 2001; pp. 170-177.
Lezzi et al., Synthesis of Thiol Chelating Resins and Their Adsorption Properties towards Heavy Metal Ions, Journal of Polymer Science: Part A: Polymer Chemistry, 1994, 32, 1877-1883.
Jiang et al., Surface Functionalization of Polyethylene for Magnetic Resonance Signal-Enhancing Coating Materials, Chem. Mater., 2002, 14, 1914-1920.
Lauer et al., Development and Characterization of Ni-NTA-Bearing Microspheres, Cytometry, 2002, 48, 136-145.
Dragsten et al: "First human studies with a high-molecular-weight iron chelator" Journal of Laboratory and Clinical Medicine, Mosby, Inc. US, vol. 135, No. 1; Jan. 1, 2000, pp. 57-65.
Liu Zu Dong et al: "Structure-activity investigation of the inhibition of 3-hydroxypyridin-4-ones on mammalian tyrosine hydroxylase"; Biochemical Pharmacology, vol. 61, No. 3; Feb. 1, 2001, pp. 285-290.
Rossi Nicholas A A et al: "In vitro chelating, cytotoxicity, and blood compatibility of degradable poly(ethylene glycol)-based macromolecular iron chelators"; Biomaterials, vol. 30, No. 4; Feb. 4, 2009, pp. 638-648.
Shriver, et al.; Inorganic Chemistry, Second Edition, 1994, Oxford University Press, pp. 321-322.
Chen, et al.; Polyethylene glycol and solutions of polyethylene glycol as green reaction media, Green. Chem, 2005, 7, pp. 64-82.
Hancock, et al., Ligand Design for Selective Complexation of Metal Ions in Aqueous Solution, Chem. Rev., 1989, 89 (8), pp. 1875-1914.
The Acidity of Organic Acids, http://www.chemguide.co.uk/basicorg/acidbase/acids.html, 11 pages, retrieved from the Internet Dec. 23, 2011.

\* cited by examiner

*Primary Examiner* — Michael G Hartley
*Assistant Examiner* — Melissa Perreira
(74) *Attorney, Agent, or Firm* — Schmeiser, Olsen & Watts, LLP

(57) ABSTRACT

A chelation structure and method of forming and using the chelation structure. The chelation structure has a backbone that includes a linear sequence of monomeric backbone units, at least one polymer side chain, and at least one chelator side chain. The side chains are each covalently coupled to the backbone at one of the monomeric backbone units by a bond that is independently biodegradable or non-biodegradable. The chelation structure is synthesized by Radical Addition Fragmentation Transfer (RAFT), Atom Transfer Radical Polymerization (ATRP), or Free Radical Polymerization (FRP). The chelation structure, individually or in combination with a shuttle chelator, may be introduced into a mammal to bind an amount of a substance in a mammal, the substance being at least one of a metal and heme. The chelation structure has a log stability constant exceeding that of the shuttle chelator for binding the substance within cells of the mammal.

40 Claims, 21 Drawing Sheets

| Chelator (L) | Metal/Heme Bound | Log Stability Constant |
|---|---|---|
| Gly-His-Lys (GHK) | Cu, Fe | 19.9 |
| 2,3-Dihydroxybenzoic acid (2,3-DHB) | Cu, Fe, Co, Zn, Mn, U, Hg, Ga | 35.7 |
| Pyridoxal isonicotinoyl hydrazone (PIH) and its derivatives | Cu, Fe, Co, Zn, Mn, U, Hg, Ga | |
| 2,2'-bipyridyl | Cu, Fe, Co, Zn, Mn, U, Hg, Ga | 17.4 [Fe(II)] |
| 1,2-dimethyl-3-hydroxypyrid-4-one & derivatives (*e.g.*, CP20) | Cu, Fe, Co, Zn, Mn, U, Hg, Ga | 26.8 |
| 1-hydroxypyridine 2-one | Cu, Fe, Co, Zn, Mn, U, Hg, Ga | 27 |
| CP502 | Cu, Fe, Co, Zn, Mn, U, Hg, Ga | 34.3 |
| ICL670 | Cu, Fe, Co, Zn, Mn, U, Hg, Ga | 38.6 |
| Dexrazoxane (ADR-925) | Cu, Fe, Co, Zn, Mn, U, Hg, Ga | 18.2 |
| *N,N*-bis(2-hydroxybenzyl)ethylenediamine-*N,N*-diacetic acid (HBED) | Cu, Fe, Co, Zn, Mn, U, Hg, Ga | 40.0 |
| O-Trensox | Cu, Fe, Co, Zn, Mn, U, Hg, Ga | 30.9 |
| Desferrioxamine (DFO; Desferal; Desferroxamine) | Cu, Fe, Co, Zn, Mn, U, Hg, Ga | 30.6 (Fe) |
| Hemopexin (endogenous compound) | Fe and Heme | |
| Chloroquine (CQ) and Chloroquine Derivatives | Fe and Heme | 6.51 [CQ; Fe(II)-Heme] |
| Penicillamine | Fe, Cu, Mn | |

*FIG. 4*

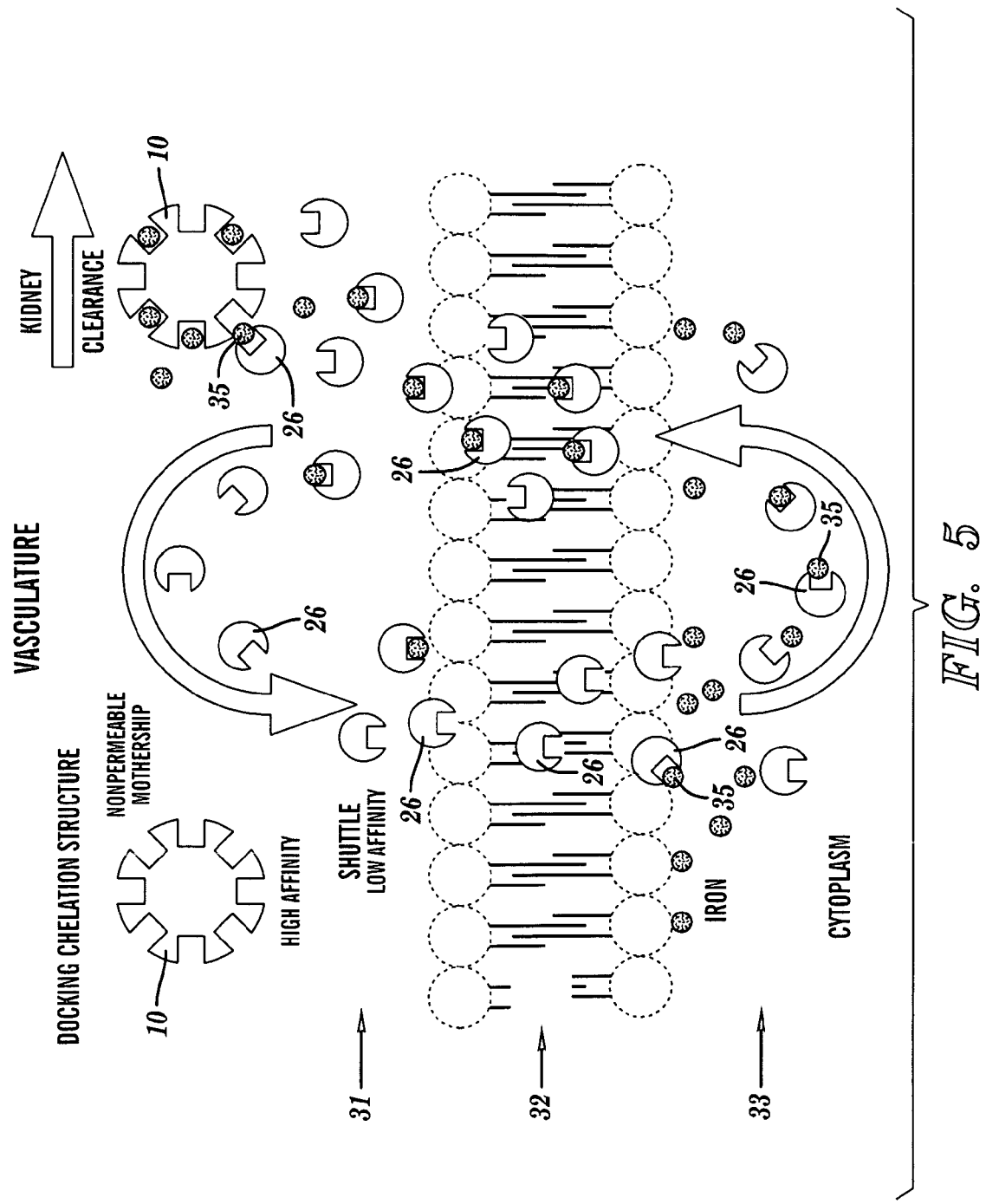

HIGH MOLECULAR WEIGHT CHELATION STRUCTURE

BACKGROUND OF THE INVENTION

1. Technical Field

The present invention relates to a chelation structure, a method of forming the chelation structure, and a method of using the chelation structure to bind metal and/or heme in a mammal.

2. Related Art

Current metal chelators are beset by problems of toxicity, short vascular retention time, and high cost. These problems are exemplified by Desferal® (DFO; also commonly referred to as desferrioxamine methane sulphonate, or simply desferrioxamine) whose chemical name is N-[5-(3-[(5-aminopentyl)-hydroxycarbamoyl]-propionamido)pentyl]-3-([5-(N-hydroxyacetamido)-pentyl]-carbamoyl)-propionohydroxamic acid monomethane sulphonate). Desferal® has been used clinically since the late 1960's and remains the drug of first choice for iron chelation despite it's high cost. The therapeutic dosage of desferal® is sufficient to cause significant injury to the patient receiving the compound which can be demonstrated by growth retardation, peripheral neuropathies, and, in mice, LD50's (~250 mg/kg) only slight above that of the typical therapeutic dosage (20-60 mg/kg) in humans. It is estimated that DFO therapy costs the typical thalassemic patient in excess of $10,000/year in US dollars.

The toxicity of current metal chelators derives, in part, from the ability of these chelator compounds to diffuse rapidly into cells and chelate essential intracellular metal (e.g., iron) stores. In the absence of these essential trace metals, the viability of the cell is adversely affected. Between the loss of the chelator into cells and their rapid clearance via the kidney, the vascular retention time of current chelators is also very poor. Again, this is readily exemplified by DFO. Upon intravascular administration, DFO undergoes complete clearance from the vasculature within approximately 20 minutes due to cellular uptake and kidney clearance.

Thus, there is a need for a metal chelator that causes less toxicity and is characterized by increased vascular retention time in comparison with current metal chelators in the prior art.

SUMMARY OF THE INVENTION

The present invention provides a chelation structure, comprising:

a backbone structured as $R_0\text{-}(A_1\text{-}A_2\text{-}\ldots\text{-}A_N)\text{-}R_1$, wherein $N \geq 2$, wherein $A_1\text{-}A_2\text{-}\ldots\text{-}A_N$ is a linearly connected sequence of N monomeric backbone units, wherein for A representing one of $A_1, A_2, \ldots A_N$, -A- is structured as

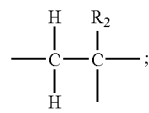

bonding structures (B) each covalently bonded to a corresponding monomeric backbone unit A in a form of A-B, wherein A-B is structured as

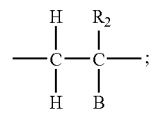

at least one water-soluble polymer structure (P), wherein each polymer structure P is covalently coupled to the corresponding monomeric backbone unit A by a corresponding bonding structure ($B_P$) of the bonding structures (B) according to $A\text{-}B_P\text{-}P$ such that $B_P\text{-}P$ is a polymer side chain covalently bonded to the backbone at A, and wherein $B_P$ is independently biodegradable or non-biodegradable for each polymer side chain $B_P\text{-}P$;

at least one chelator (L), wherein each chelator L is covalently coupled to the corresponding monomeric backbone unit A by a corresponding bonding structure ($B_L$) of the bonding structures (B) such that $B_L\text{-}L$ is a chelator side chain covalently bonded to the backbone at A, and wherein $B_L$ is independently biodegradable or non-biodegradable for each P chelator side chain $B_L\text{-}L$;

wherein $R_0$ and $R_1$ are independently selected from the group consisting of a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, and an epoxide group;

wherein for each monomeric unit, $R_2$ is independently selected from the group consisting of a hydrogen group, an alkyl group, a benzyl group, and an aryl group;

wherein for each polymer side chain, P is independently selected from the group consisting of a poly(ethylene glycol) (PEG) structure, a poly(propylene glycol) group, a poly(acrylamide) group, a N-substituted polyacrylamides group, a carbohydrate polymer group, an oligosaccharide group, a polyvinyl alcohol group, a polyglycerol group, and a polyvinylpyrolidone group; and wherein for each chelator side chain, the chelator L has a log stability constant $K_L$ no less than 15 for binding a substance selected from the group consisting of at least one metal, heme, and a combination thereof.

The present invention provides a method for forming a chelation structure, said method comprising synthesizing the chelation structure, said chelation structure comprising:

a backbone structured as $R_0\text{-}(A_1\text{-}A_2\text{-}\ldots\text{-}A_N)\text{-}R_1$, wherein $N \geq 2$, wherein $A_1\text{-}A_2\text{-}\ldots\text{-}A_N$ is a linearly connected sequence of N monomeric backbone units, wherein for A representing one of $A_1, A_2, \ldots A_N$, -A- is structured as

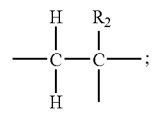

bonding structures (B) each covalently bonded to a corresponding monomeric backbone unit A in a form of A-B, wherein A-B is structured as

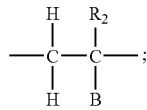

at least one water-soluble polymer structure (P), wherein each polymer structure P is covalently coupled to the corresponding monomeric backbone unit A by a corresponding bonding structure ($B_P$) of the bonding structures (B) according to A-$B_P$-P such that $B_P$-P is a polymer side chain covalently bonded to the backbone at A, and wherein $B_P$ is independently biodegradable or non-biodegradable for each polymer side chain $B_P$-P;

at least one chelator (L), wherein each chelator L is covalently coupled to the corresponding monomeric backbone unit A by a corresponding bonding structure ($B_L$) of the bonding structures (B) such that $B_L$-L is a chelator side chain covalently bonded to the backbone at A, and wherein $B_L$ is independently biodegradable or non-biodegradable for each P chelator side chain $B_L$-L;

wherein $R_0$ and $R_1$ are independently selected from the group consisting of a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, and an epoxide group;

wherein for each monomeric unit, $R_2$ is independently selected from the group consisting of hydrogen group, an alkyl group, a benzyl group, and an aryl group;

wherein for each polymer side chain, P is independently selected from the group consisting of a poly(ethylene glycol) (PEG) structure, a poly(propylene glycol) group, a poly(acrylamide) group, a N-substituted polyacrylamides group, a carbohydrate polymer group, an oligosaccharide group, a polyvinyl alcohol group, a polyglycerol group, and a polyvinylpyrolidone group; and wherein for each chelator side chain, the chelator L has a log stability constant $K_L$ no less than 15 for binding a substance selected from the group consisting of at least one metal, heme, and a combination thereof.

The present invention provides chelation method for reducing an amount of a substance in a mammal, said method comprising introducing a chelation structure into the mammal, said chelation structure comprising:

a backbone structured as $R_0$-($A_1$-$A_2$-....-$A_N$)-$R_1$, wherein N≧2, wherein $A_1$-$A_2$- . . . -$A_N$ is a linearly connected sequence of N monomeric backbone units, wherein for A representing one of $A_1$, $A_2$, ... $A_N$, -A- is structured as

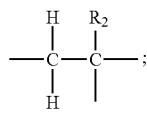

bonding structures (B) each covalently bonded to a corresponding monomeric backbone unit A in a form of A-B, wherein A-B is structured as

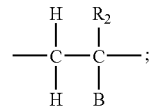

at least one water-soluble polymer structure (P), wherein each polymer structure P is covalently coupled to the corresponding monomeric backbone unit A by a corresponding bonding structure ($B_P$) of the bonding structures (B) according to A-$B_P$-P such that $B_P$-P is a polymer side chain covalently bonded to the backbone at A, and wherein $B_P$ is independently biodegradable or non-biodegradable for each polymer side chain $B_P$-P;

at least one chelator (L), wherein each chelator L is covalently coupled to the corresponding monomeric backbone unit A by a corresponding bonding structure ($B_L$) of the bonding structures (B) such that $B_L$-L is a chelator side chain covalently bonded to the backbone at A, and wherein $B_L$ is independently biodegradable or non-biodegradable for each P chelator side chain $B_L$-L;

wherein $R_0$ and $R_1$ are independently selected from the group consisting of a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, and an epoxide group;

wherein for each monomeric unit, $R_2$ is independently selected from the group consisting of a hydrogen group, an alkyl group, a benzyl group, and an aryl group;

wherein for each polymer side chain, P is independently selected from the group consisting of a poly(ethylene glycol) (PEG) structure, a poly(propylene glycol) group, a poly(acrylamide) group, a N-substituted polyacrylamides group, a carbohydrate polymer group, an oligosaccharide group, a polyvinyl alcohol group, a polyglycerol group, and a polyvinylpyrolidone group; and wherein for each chelator side chain, the chelator L has a log stability constant $K_L$ no less than 15 for binding the substance, said substance being selected from the group consisting of at least one metal, heme, and a combination thereof.

The present invention advantageously provides a metal chelator that causes less toxicity and is characterized by increased vascular retention in comparison with current metal chelators in the prior art.

BRIEF DESCRIPTION OF THE DRAWINGS

FIG. 4 is a table depicting metal chelators which may be utilized in the chelation structures of FIGS. 1-3, in accordance with embodiments of the present invention.

FIG. 5 depicts a shuttle chelator system, in accordance with embodiments of the present invention.

DETAILED DESCRIPTION OF THE INVENTION

The detailed description of the invention is divided into the following sections:
1. Structure and Function of the Chelation Structure;
2. Synthesis of the Chelation Structure; and
3. Validation of Chelation Structure Functionality.

1. Structure and Function of the Chelation Structure

Figure 1:
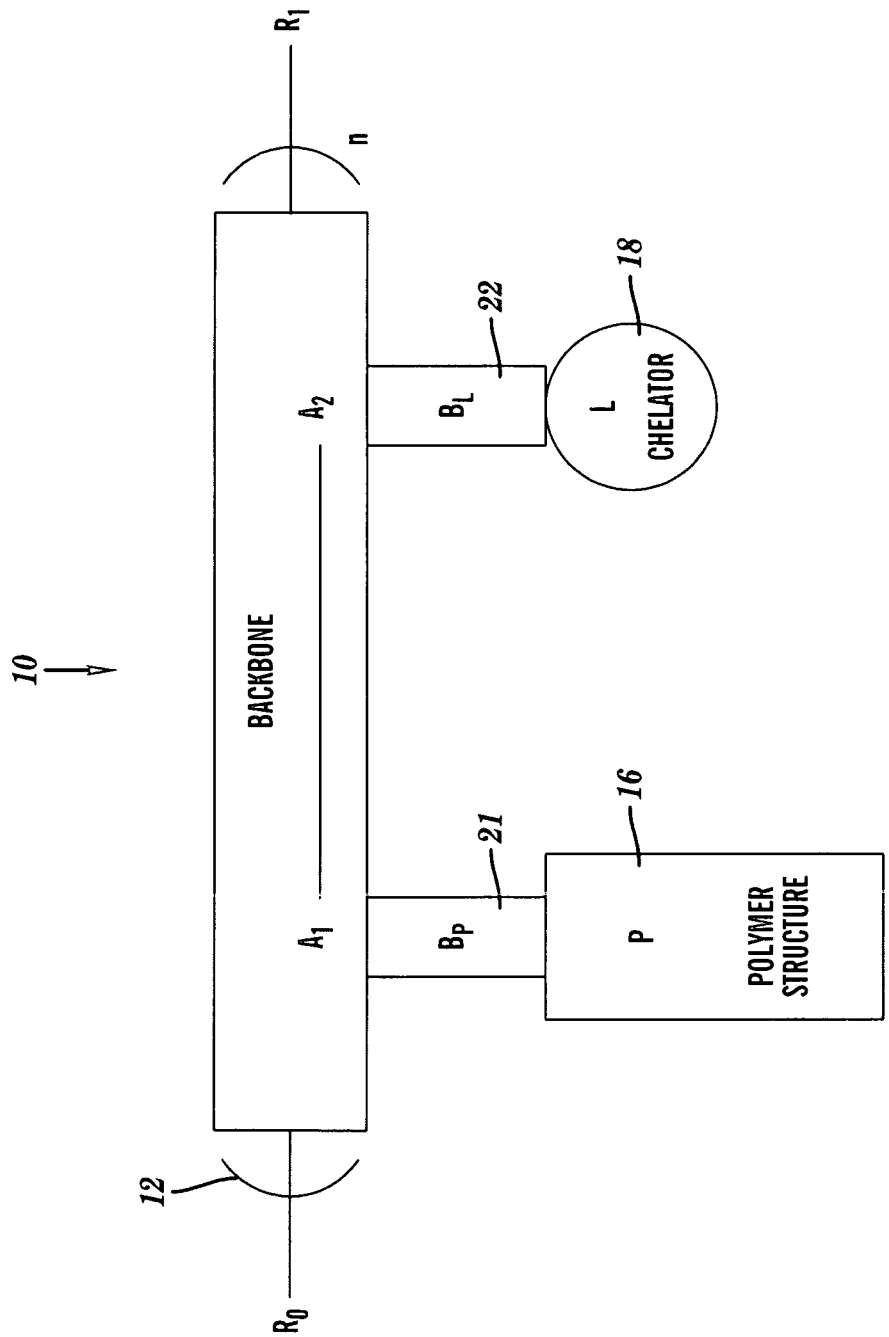
FIGS. 1-3 depict chelation structures, in accordance with embodiments of the present invention.
Figure 2:
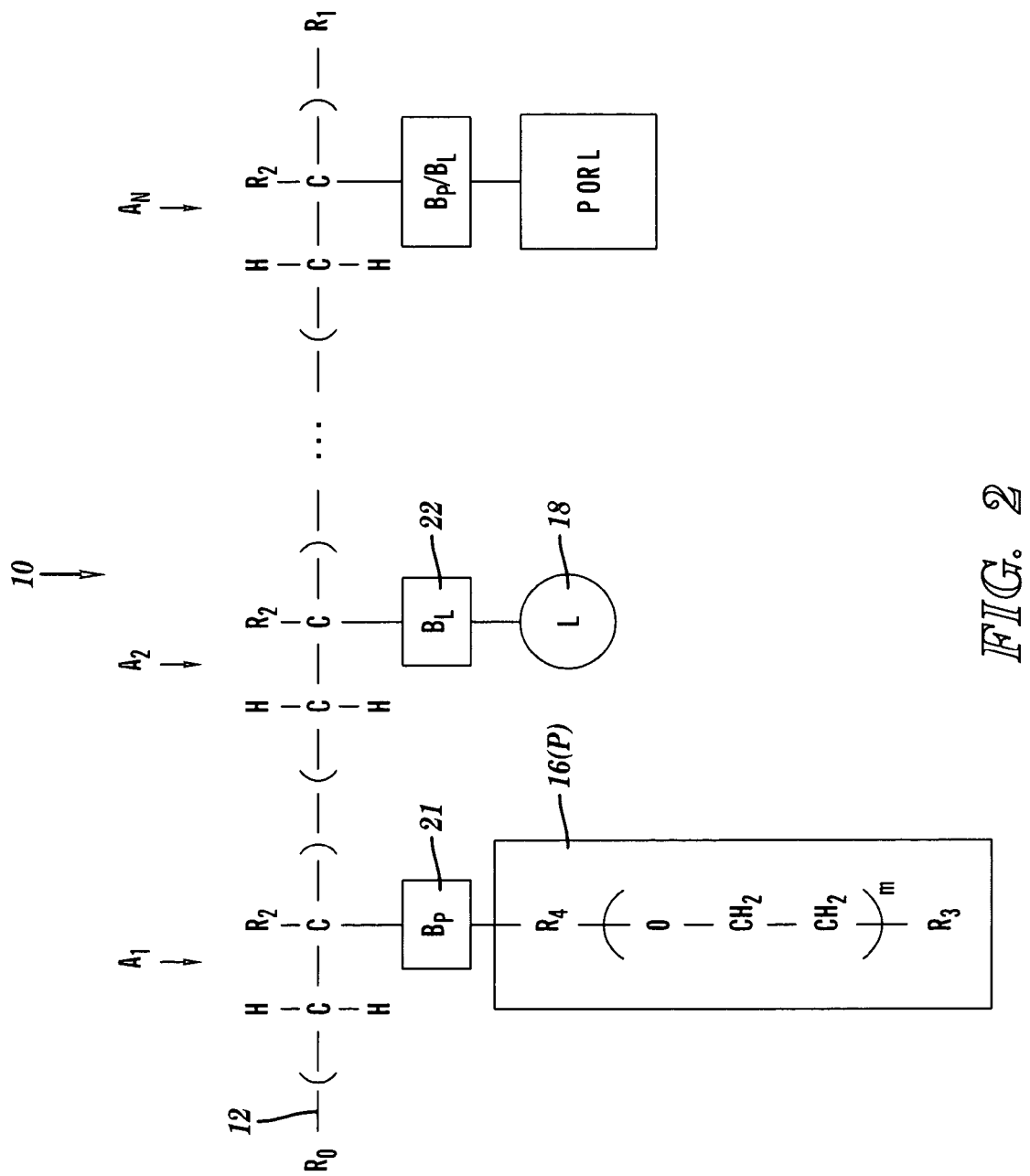
Figure 3:
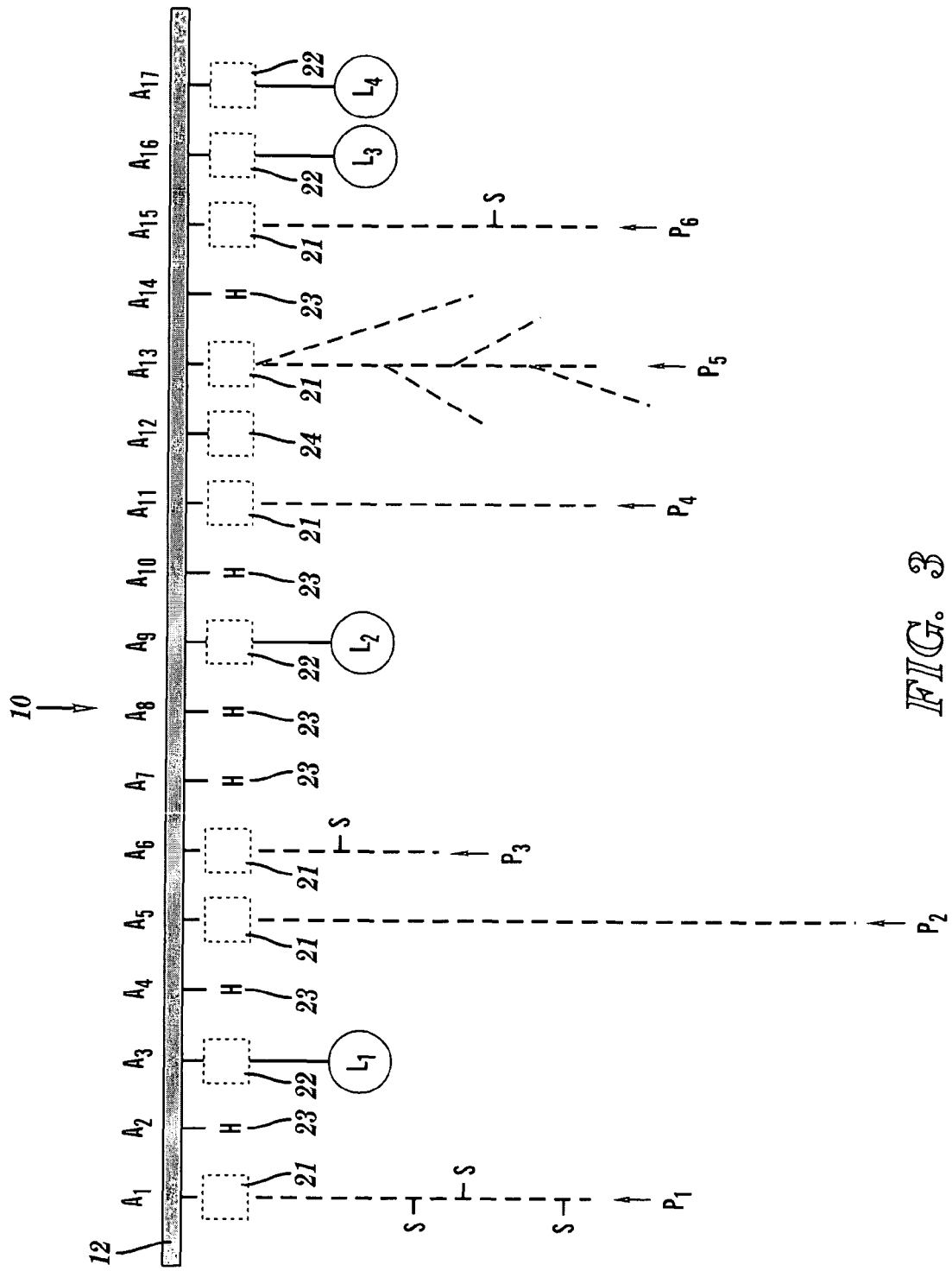

FIGS. 1-3 depict a chelation structure 10, in accordance with embodiments of the present invention. FIGS. 1-3 show different details of the chelation structure 10.

FIG. 1 depicts the chelation structure 10 as comprising the modular components of a backbone 12, bonds 21 and 22, a water-soluble polymer structure (P) 16, and a chelator (L) 18. The backbone 12 is a linear polymer comprising n units represented as $(A_1\text{-}A_2)_n$, wherein $A_1$ and $A_2$ are monomeric backbone units, and wherein n is a positive integer in the range $1 \leq n \leq \infty$. The linear polymer may be a block copolymer or a terpolymer. $A_1$ and $A_2$ independently comprise the structural form shown in FIG. 2, described infra. In one embodiment, the backbone has a molecular weight in a range of 200 to 50000 daltons.

The backbone 12 also comprises end groups $R_0$ and $R_1$. $R_0$ and $R_1$ may each independently comprise a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, or an epoxide group.

Bonds 21 (denoted as $B_P$) and 22 (denoted as $B_L$) are covalently bonded to corresponding monomeric backbone units $A_1$ and $A_2$, respectively, and also to the polymer structure 16 and the chelator 18, respectively. Bond 21 and polymer structure 16 collectively form a polymer side chain attached to the backbone 12 at monomeric backbone unit $A_1$. Bond 22 and chelator 18 collectively form a chelator side chain attached to the backbone 12 at monomeric backbone unit $A_2$. Bonds 21 and 22 are independently biogradable (denoted as B1 if biogradable) or non-biogradable (denoted as B2 if non-biogradable). Each biodegradable bond B1 may independently comprise an ester group, a substituted esters group, a disulfide group, a substituted disulfide group, an acetal group, a ketal group, a glycoside group, an anhydride group, a peptide group, or a urethane group. Each non-biodegradable bonds B2 may independently comprise a N-substituted amide group, a benzyl group, an aryl group, an alkyl group, or an ether group.

Polymer structure 16 (P) can contain one or more reactive sites (depicted as $R_4$, and $R_3$ in FIG. 2, and as S in FIG. 3) which can be used to provide added functionality to the aggregate chelation structure 10. Chelator 18 (denoted as L) is adapted to bind a substance (e.g., a metal or heme). Examples of chelators represented by L are depicted in FIG. 4, described infra. The combination of the backbone 12 and one or more polymer structure 16 serves as a molecular carrier for the chelator 18. The chelator 18 provides the active metal binding site of the chelation structure 10. As shown, each monomeric backbone unit (i.e., $A_1, A_2, \ldots$) can be covalently coupled (via bond 21 or 22) to either the polymer structure 16 or the chelator 18.

As the molecular weight of the backbone 12 increases, the number of reactive sites (e.g., $A_1$ and $A_2$) along the backbone 12 increase correspondingly and can serve as attachment sites for additional polymer side chains and/or chelator 18 side chains, using either biodegradable (B1) or non-biodegradable (B2) covalent bonds. The biodegradable and non-biodegradable characteristic of bonds B1 and B2, respectively, affects the clearance rate of the chelation structure 10 from the vascular space of a mammal into which the chelation structure 10 has been introduced. The mammal may be a human being or a non-human mammal. B1 (biodegradable) bonds will allow for more rapid clearance while B2 (non-biodegradable) bonds will result in enhanced vascular retention. Each bond 21 and 22 along the backbone 12 is independently biodegradable (B1) or non-biodegradable (B2). Variable combinations of biodegradability and non-biodegradabillity (i.e., of B1 and B2) can be present in the chelation structure 10.

The chelation structure 10 has a relatively high molecular weight as compared with the molecular weight of the chelator 18 (L), due to the aggregate molecular weight of the backbone 12 and polymer structure 16. The combined molecular weight and composition of the backbone 12 and polymer structure 16 governs the Stokes radius of the chelation structure 10. As defined, the Stokes radius of a molecule is the effective radius of the molecule as the molecule tumbles rapidly in solution. A long, extended molecule has a larger Stokes radius than a compact molecule. Because of this relationship, the Stokes radius of the invention is increased as the number of monomeric backbone units (i.e., $A_1, A_2, \ldots$) in the backbone 10 is increased, and as size of the polymer structure 16 attached to the monomeric backbone unit $A_1$ increases. Thus, the molecular weight of the backbone 12 and/or the polymer structure 16 (P) can be manipulated to increase or decrease the aggregate molecular weight of the chelation structure 10, and to increase or decrease the Stokes radius of the chelation structure 10.

While FIG. 1 depicts two monomeric backbone units $A_1$ and $A_2$, the backbone 12 may generally comprise N such monomeric backbone units for any positive integer N of at least 2, as illustrated in FIG. 2.

FIG. 2 depicts the chelation structure 10 of FIG. 1, wherein specific chemical structures are shown for $A_1$, $A_2$, and P as shown. Letting A represent one of the monomeric backbone units $A_1, A_2, \ldots, A_N$ subject to $N \geq 2$, the structure -A- is represented as:

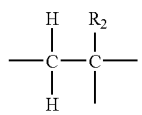

Letting B represent $B_P$ or $B_L$ (wherein $B_P$ and $B_L$ are each independently biodegradable or non-biodegradable as discussed supra), the structure A-B is represented as:

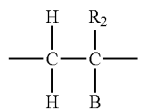

$R_2$ may independently differ or not differ in different monomeric units $A_1, A_2, \ldots, A_N$ along the backbone 12. In each monomeric backbone unit A, $R_2$ may independently comprise a hydrogen group, an alkyl group, a benzyl group, or an aryl group.

The chelator 18 (L) is covalently coupled to monomeric backbone unit $A_2$ via bond 22 as in FIG. 1.

The polymer structure 16 has the structural form of $R_4$—$(R_5)_m R_3$, wherein m is a positive integer in the range $1 \leq m \leq \infty$. The polymer structure 16 is a poly(ethylene glycol) (PEG) group if $R_4$ is $CH_2$—$CH_2$, $R_5$ is O—$CH_2$—$CH_2$, and $R_3$ is OH (i.e., a PEG group is $CH_2$—$CH_2$—(O—$CH_2$—$CH_2$—$)_m$OH). The polymer structure 16 is a modified PEG group if $R_4$ is modified $CH_2$—$CH_2$ and/or $R_5$ is substituted O—$CH_2$—$CH_2$ as described infra. The polymer structure 16 is a "PEG structure" if the polymer structure 16 is a PEG group or a modified PEG group.

$R_4$ is covalently bonded to both the repeating units (O—$CH_2$—$CH_2$)$_m$ and the bond ($B_P$) 21 in a structural configuration of $B_P$-$R_4$—(O—$CH_2$—$CH_2$—$)_m R_3$. $R_4$ may be $CH_2$—$CH_2$ or modified $CH_2$—$CH_2$. Modified $CH_2$—$CH_2$ is substituted $CH_2$—$CH_2$, expanded $CH_2$—$CH_2$, or truncated $CH_2$—$CH_2$. Substituted $CH_2$—$CH_2$ has a group replacement for at least one H in $CH_2$—$CH_2$, such as $CH_2$—CH(OH)—. Expanded $CH_2$—$CH_2$ has at least one group added to $CH_2$—$CH_2$ (e.g., $CH_2$—$CH_2$—N— having an added nitrogen group). Truncated $CH_2$—$CH_2$ is $CH_2$—.

$R_5$ is represented as O—$CH_2$—$CH_2$ in FIG. 2. $R_5$ may denote substituted O—$CH_2$—$CH_2$. Substituted O—$CH_2$—$CH_2$ has a group replacement for at least one H in O—$CH_2$—$CH_2$. The substituted O—$CH_2$—$CH_2$ may include: —O—$CH_2$—CH($CH_2$—O)—O—.

Generally, $R_3$ may include a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, an epoxide group, a halide group, an amino acid group, a carbohydrate group, or a peptide group.

Generally, P is one of a poly(ethylene glycol) (PEG) structure, a poly(propylene glycol) group, a poly(acrylamide) group, a N-substituted polyacrylamides group, a carbohydrate polymer group, an oligosaccharide group, a polyvinyl alcohol group, a polyglycerol group, or a polyvinylpyrolidone group.

Note that P is of the form $R_4$—$(R_5)_m R_3$ if P is a PEG structure, as described supra.

FIG. 3 depicts the chelation structure 10 of FIG. 2 for depicting the monomeric backbone units $A_1, A_2, A_3, \ldots, A_{17}$ sequenced along the backbone 12. Each of the monomeric backbone units $A_1, A_2, A_3, \ldots, A_{17}$ has the chemical structure that is depicted for $A_1, A_2,$ and $A_N$ in FIG. 2. Some monomeric backbone units ($A_2, A_4, A_7, A_8, A_{10}, A_{14}$) do not have an attached side chain, but instead have hydrogen (H) 23 attached thereto. Moreover, the monomeric backbone unit $A_{12}$ is attached to bond 24 but does not have hydrogen or a side chain attached thereto. As shown, bond $B_P$ 21 of the polymer side chain, bond $B_L$ 22 of the chelator side chain, the hydrogen (H) 23, and bond 24 are sequenced in the order of 21, 23, 22, 23, 21, 21, 23, 23, 22, 23, 21, 24, 21, 23, 21, 22, 22 as attached to the monomeric backbone units $A_1, A_2, A_3, A_4, A_5, A_6, A_7, A_8, A_9, A_{10}, A_{11}, A_{12}, A_{13}, A_{14}, A_{15}, A_{16}, A_{17}$, respectively, along the backbone 12. In general, the polymer side chains, the chelator side chains, the attached hydrogen (H), and bonds without attached hydrogen or side chains may be sequenced in a random order, or in any predetermined order, along the backbone 12, via exercise of appropriate controls (e.g., the amount of each component used for the polymerization, copolymerization reactivity ratio of each component, temperature, ionic strength, pH, catalyst composition, catalyst concentration, catalyst reactivity, and solvent composition) during the synthesis of the chelation structure 10 as explained infra. As shown in FIG. 3, the polymer structures may be linear (e.g., $P_1, P_2, P_3, P_4, P_6$) or branched (e.g., $P_5$). The bonds 21, 22, and 24 may be independently biodegradable or non-biodegradable. Although not shown in FIG. 3, the polymer structures comprise end groups $R_4$ and $R_3$ as discussed supra in conjunction with FIG. 2.

In one embodiment, $R_2$ (see FIG. 2) is a same group for all of said monomeric backbone units $A_1, A_2, A_3, \ldots, A_{17}$. In one embodiment, $R_2$ is a different group for at least two monomeric backbone units of monomeric backbone units $A_1, A_2, A_3, \ldots, A_{17}$.

In FIG. 3, the polymer structures $P_1, P_3,$ and $P_6$ have replacement structures S in modification of the repeating units O—$CH_2$—$CH_2$ (see FIG. 2). The presence of S denotes that S replaces a hydrogen (H) in the repeating units O—$CH_2$—$CH_2$, which transforms O—$CH_2$—$CH_2$ to a substituted O—$CH_2$—$CH_2$. One or more such replacement structures S may replace H in one or more repeating units O—$CH_2$—$CH_2$. The polymer structures $P_2, P_4,$ and $P_5$ do not have such replacement structures S within the repeating units O—$CH_2$—$CH_2$. In one embodiment, S may substitute for H in $R_3$ (see FIG. 2).

In one embodiment, S is such that one or more polymer side chains confer special functionality (fluorescent tag, radiolabel, etc.). In one embodiment, S is such that one or more polymer side chains improve biocompatibility in linear polymer structures (e.g., $P_1, P_2, P_3, P_4, P_6$) and/or branched polymer structures (e.g., $P_5$). In one embodiment, S is such that one or more polymer side chains facilitate transport of the chelation structure 10 to a specified body site within a mammal after the chelation structure 10 has been introduced into the mammal.

In one embodiment, each polymer structure independently has a molecular weight in a range of 200 to 50000 daltons.

FIGS. 10-19 depict chelation structures showing different combinations of monomeric backbone units and biodegradable/non-biodegradable linkages between the backbone and both the polymer side chains and the chelator side chains, in accordance with embodiments of the present invention. In FIGS. 10-19, the polymer side chains are poly(ethylene glycol) (PEG) side chains. In FIGS. 10-19, the monomeric backbone units linked to the PEG side chains, and the chelator side chains have group R2(P) and R2(L) respectively representing $CH_3$ and $CH_3$ in FIG. 10. The PEG side chains and the chelator side chains are attached to the monomeric backbone units via bonds $B_P$ and $B_L$, respectively, wherein the bonds $B_P$ and $B_L$ the bonds may independently be biodegradable (B1) or non-biodegradable (B2), as shown infra in Table 1.

TABLE 1

| FIG. | $B_P$ | $B_L$ | R2(P) | R2(L) |
|---|---|---|---|---|
| 10 | B1 | B1 | $CH_3$ | $CH_3$ |
| 11 | B1 | B1 | H | H |
| 12 | B1 | B1 | $CH_3$ | H |
| 13 | B1 | B1 | H | $CH_3$ |
| 14 | B1 | B2 | H | $CH_3$ |
| 15 | B2 | B1 | H | $CH_3$ |
| 16 | B2 | B2 | H | $CH_3$ |
| 17 | B2 | B2 | $CH_3$ | $CH_3$ |
| 18 | B2 | B2 | H | H |
| 19 | B2 | B2 | $CH_3$ | H |

FIG. 4 is a table depicting chelators which may be utilized in the chelation structures 10 of FIGS. 1-3, in accordance with embodiments of the present invention. For each chelator (L) listed, FIG. 4 indicates substances (i.e., metal(s) and/or heme) that may be bound to the chelator according to the metal/heme's affinity to the chelator. The affinity of the metal/heme to the chelator is governed by K, wherein K is the log stability constant for the binding of the metal/heme to the chelator. Stability of a complex in solution refers to the degree of association between the two species involved in the state of equilibrium (e.g., iron and chelator). Qualitatively, the greater the association between metal and chelator, the greater will be the stability of the complex in solution. The magnitude of the equilibrium constant (stability or formation) for the association, quantitatively expresses the stability. Usually the metal-chelator binding process is represented by a series of stepwise equilibria which lead to stability constants that may vary numerically from hundreds to enormous values such as $10^{35}$ and more. For this reason, the logarithm of the stability, rather than the stability itself, is commonly reported. In one embodiment the chelator (L) has a log stability constant no less than about 15. The chelators in FIG. 4 are merely illustrative and numerous other transition metal chelators can be similarly utilized.

In one embodiment in FIG. 4, the metal(s) to be bound to the chelator (L) may comprise at least one of Cu, Fe, Co, Zn, Mn, U, Kg, and Ga, wherein the chelator may comprise at least one of: Gly-His-Lys (GHK); 2,3-Dihydroxybenzoic acid; Pyridoxal isonicotinoyl hydrazone (PIH) and derivatives thereof; 2,2'-bipyridyl; 1,2-dimethyl-3-hydroxypyrid-4-one and derivatives thereof; 1-hydroxypyridine 2-one; CP502; 4-[3,5-bis(2-hydroxyphenyl)-1,2,4-triazol-1-yl]-benzoic acid (ICL670); Dexrazoxane (ADR-925); N,N-bis (2-hydroxybenzyl)ethylenediamine-N,N-diacetic acid (HBED); O-Trensox; and Desferrioxamine (DFO).

In one embodiment in FIG. 4, the metal(s) and/or heme to be bound to the chelator (L) may comprise at least one of Fe and heme, wherein the chelator may comprise at least one of Hemopexin, Chloroquine (CQ), and Chloroquine derivatives.

In one embodiment in FIG. 4, the metal(s) to be bound to the chelator (L) may comprises at least one of Fe, Cu, and Mn, wherein the chelator may comprise Penicillamine.

Current clinical needs for chelators are typically focused on iron (Fe) and copper (Cu) as both of these essential trace metals are associated with common pathological conditions.

A wide variety of transition metals (e.g., uranium (U), mercury (Hg)), however, have been shown to exert significant toxicity both in vitro and in vivo. Metal toxicity can arise from acute ingestion (e.g., iron tablets), heredity (e.g., hemachromatosis (Fe); Wilson's disease (Cu)), or consequent to chronic transfusion therapy (i.e., secondary iron overload) or chronic environmental/industrial exposure (e.g., Hg, U).

The chelators listed in FIG. 4, and generally the chelator 18 (L) used in the chelation structure 10 of the present invention, have a significantly lower molecular weight than does the overall chelation structure 10 of the present invention, due to the potentiality of relatively high molecular weight contributions from backbone 12 and the polymer structures 16. For example, ICL670 has a molecular weight of 373.4 daltons and HBED has a molecular weight of 386 daltons. In contrast in the present invention, the backbone 12 may have molecular weight in a range of 200 to 50000 daltons, and each polymer structure 16 may have molecular weight in a range of 200 to 50000 daltons.

FIG. 5 depicts a shuttle chelator system, in accordance with embodiments of the present invention. FIG. 5 depicts a cellular environment (e.g., an environment of a red blood cell) comprising a cell membrane 32 interposed between an extracellular space 31 and intracellular space 33. The shuttle chelator system of FIG. 5 employs both the chelation structure 10 (described supra in conjunction with FIGS. 1-3) and shuttle chelators 26. The shuttle chelators 26 are essentially the same chelators as the chelators 18 in FIGS. 1-3, except that the shuttle chelators 26 are free and not integrated into the chelation structure 10 as are the chelators 18. FIG. 4 provides examples of the shuttle chelators 26. In the shuttle chelator system of FIG. 5, the chelation structure 10 is called a "docking chelation structure".

The shuttle chelators 26 have a relatively low molecular weight in comparison with the molecular weight of the chelation structure 10 as explained supra. The relatively low molecular weight of the shuttle chelators 26 makes the shuttle chelators 26 cell permeable; i.e., capable of migrating through the cell membrane 32 so as to move from the extracellular space 31 to the intracellular space 33, and from the intracellular space 33 to the extracellular space 31. The shuttle chelators 26 may enter the intracellular space 33 of the cell through the membrane 32 via random diffusion but may alternatively enter the intracellular space 33 via an active process. In the intracellular space 33 of the cell, the shuttle chelators 26 bind metal(s)/heme 35 wherein the metals 35 are free or loosely complexed and capable of causing cell injury. Examples of such metals 35 are listed in FIG. 4.

In contrast, the relatively high molecular weight of the chelation structure 10 inhibits the chelation structure 10 from migrating through the cell membrane 32. Thus, the chelation structure 10 is disposed primarily in the extracellular space 31.

After binding the metal(s)/heme 35, the shuttle chelators 26 leave the intracellular space 33 (via random diffusion or by an active process) and enter the vascular or extracellular space 31 after passing through the cell membrane 32. Within the vascular or extracellular space 31, the chelation structure 10 has a higher affinity for the metal(s)/heme than does the shuttle chelator 26 (i.e., the log stability constant $K_L$ of the chelator L 18 in the docking chelation structure 10 exceeds the log stability constant $K_S$ of the shuttle chelator 26). Therefore in the vascular or extracellular space 31, the chelation structure 10 subsequently pulls and then binds (i.e., chelates) the metal(s)/heme 35 from the shuttle chelators 26 and are subsequently cleared, along with the shuttle chelators 26, from the body (primarily via the kidneys) of the mammal.

Thus the shuttle chelator system of the present invention provides efficient removal of toxic metals to prevent/delay injury to cells (e.g., erythrocyte, hepatic cell) and organs (e.g., liver, heart, kidney, brain).

Studies over a wide range of pharmacological compounds demonstrate that, as a general principle, as the aggregate molecular weight of an agent increases, cell permeability and cellular/organismal toxicity decreases while vascular retention increases. These teachings are demonstrated by the example of free DFO and high molecular weight dextran and starch derivatives of DFO (D-DFO and S-DFO; U.S. Pat. No. 6,479,468 issued Nov. 12, 2002 to Hedlund et al.). As a consequence of the increase in molecular weight and Stokes radius of the D-/S-DFO molecule, cell permeability of the D-/S-DFO molecules is decreased. This results in dramatically reduced toxicity to cells and animals (e.g., mammals) as exemplified by the finding that the LD50 in mice of free DFO is ~250 mg/kg, while the LD50 of the S-DFO is >4000 mg DFO Equivalents/kg. Similarly, as the Stokes radius of the S-DO increases, kidney clearance and vascular retention is improved. Indeed, while DFO undergoes complete clearance from the vasculature within approximately 20 minutes, the high molecular weight D/S-DFO are detectable >5 days post injection. See Hedlund et al., U.S. Pat. No. 6,479,468 issued Nov. 12, 2002 to Hedlund et al. See, also, Dragsten P R, Hallaway P E, Hanson G J, Berger A E, Bernard B, Hedlund B E (2000), First human studies with a high-molecular-weight iron chelator, J Lab Clin Med. 135:57-65.

An underlying biophysical mechanism relating to the inverse relationship between molecular weight and cell toxicity, cell permeability, and renal clearance (i.e., low molecular weight results in high oxicity/cell permeability/renal clearance) relates to the Stoke's radius of the molecule. The Stokes radius is the effective radius a molecule as the molecule tumbles rapidly in solution. A long, extended molecule has a larger Stokes radius than a compact molecule, even if the extended molecule and the compact molecule have the same molecular mass. As molecular weight increases, the Stokes radius increases, though this is somewhat dependent on the packing/density of the substance (protein, polymer, etc). Furthermore, as the Stokes radius of a molecule increases, there is a reduction in cell permeability. Since cell permeability for low molecular weight chelators is associated with chelation of intracellular metals, cellular toxicity is similarly decreased. In addition, because larger molecules are more slowly cleared from the vascular space by the kidney, particles (e.g., proteins) with increasing stokes radius (related to increasing molecular weight) exhibit improved vascular retention.

The present invention utilizes the concepts described above in a novel manner to: reduce the toxicity of the low molecular weight chelators, improve vascular retention of the low molecular weight chelators, and increase water/plasma solubility of existing and future low molecular weight metal chelators for clinical use. The vascular retention time, cell permeability, water/plasma solubility and toxicity profiles of the described novel chelation structure 10 of the present invention are readily manipulated by concurrently or independently changing any or all of the following parameters: the molecular weight (size) of the backbone; the number of the polymer side chains; the size (molecular weight) of the polymer side-chains; the shape of the PEG side chains (linear vs. branched).

The backbone 12, which may be a polyacrylate or acrylamide-derived backbone, is a linear macromolecule (i.e., a polymer). The Stokes radius of a particle is the effective radius a molecule as it tumbles rapidly in solution. A long, extended molecule has a larger Stokes radius than a compact molecule. Because of this relationship, the Stokes radius of the molecule is increased according to the number (n) of monomeric backbone units) in the backbone.

The Stokes radius of the molecule is further influenced by the physical nature of polymer structure (P). The more polymer structures (P) attached to the backbone, the higher the molecular weight of the aggregate chelation structure 10 and the Stokes radius. As the molecular weight of the polymer structure (P) increases, so does the Stokes radius of the aggregate chelation structure 10. Furthermore, polymer structure (P) may be linear or branched as shown in FIG. 3. A branched polymer structure increases the Stokes radius less than a linear polymer structure of the same molecular weight, since the branched polymer structure is more compact than the linear polymer structure and interacts less with the surrounding medium. Note that the chelator (L) (e.g., as listed in FIG. 4) minimally impacts the aggregate Stokes radius of the molecule due to the relatively smaller size of the chelator (L) in comparison with the backbone 12 and/or the polymer structure (P) 16.

The manipulations described supra (i.e., the molecular weight of the backbone; the number of the polymer side chains; the molecular weight of the polymer side-chains; the shape of the polymer side chains) dramatically affect the Stokes radius of the resulting chelation structure 10 of the present invention. The increase in the Stokes radius correlates directly correlated with the in vivo vascular half-life of a pegylated compound and is inversely correlated with the rate of renal clearance, both of which govern exit of the pegylated compound from the vascular space via the kidney or into cells. See Yamaoka T, Tabata Y, Ikada Y (1994), Distribution and tissue uptake of poly(ethylene glycol) with different molecular weights after intravenous administration to mice, J Pharm Sci. 83:601-6. See, also, Jorgensen K E, Moller J V (1979), Use of flexible polymers as probes of glomerular pore size, Am J Physiol. 236:F103-11. Thus, the chelation structure 10 of the present invention is non-permeable to cells due to its large size and exerts less toxicity relative to the cell permeable low molecular weight form of the chelators of the prior art.

Thus, increasing the Stokes radius of the chelation structure 10: decreases cell permeability, decreases cell toxicity, decreases renal clearance, and increases vascular retention.

The chelation structure 10 of the present invention may have the following clinical uses, inter alia: prevention of iron-mediated free radical injury (oxidant generating drugs, ischemia reperfusion); prevention of toxicity due to other transition metal (e.g., copper, cobalt, manganese, zinc); use in primary and secondary tissue (e.g., liver, kidneys, heart, endocrine) iron overload states; use in acute iron toxicity cases (e.g., neonatal ingestion of iron supplement tablets); use in cancer therapy (iron deprivation prevents tumour cell proliferation); use in Sickle Cell Anemia (RBC injury and secondary iron overload); use in Thalassemia (RBC injury and secondary iron overload); use in brain injury (e.g., trauma, stroke, ischemia-reperfusion); use in alcohol abuse (liver toxicity due to alcohol metabolism: iron-acetaldehyde toxicity); use in the treatment of malaria; use in the treatment of neurodegenerative diseases (e.g., Parkinsons disease).

2. Synthesis of the Chelation Structure

The chelation structure 10 of the present invention may be synthesized by any of the following methods: Radical Addition Fragmentation Transfer (RAFT); Atom Transfer Radical Polymerization (ATRP); and Free Radical Polymerization (FRP).

Controlled polymerizations (examples of which include RAFT and ATRP) are based on establishing a rapid dynamic equilibrium between a small amount of reactive radical components (e.g., the polymer structure (P) 16 and the chelator (L) in the preformed polymer synthesis schemes for the present invention) and a large majority of the dormant species (A) or (A)-(P) as described supra. The dormant chains may be alkyl halides, as in ATRP, thioesters, as in reversible addition fragmentation chain transfer (RAFT) polymerization or alkoxyamines, as in nitrous oxide mediated polymerization. Conventional Free Radical polymerization (FRP) utilizes free radical species of individual subunits generated via homolysis of radical initiators. An advantage of controlled polymerization techniques such as RAFT and ATRP is that most often polymer properties such as molecular weight, molecular weight distribution and composition can be predetermined and closely controlled in contrast with free radical polymerization Thus, use of RAFT and/or ATRP facilitates a production of high molecular weight chelation structures with precise molecular parameters.

In Radical Addition Fragmentation Transfer (RAFT), radicals are generated by homolytic cleavage of a radical initiator (e.g., benozyl peroxide, azobisisobutyronitrile, azobisisovaleric acid) and addition of monomer. Chain transfer reagents (CTA) (e.g. dithioesters) will be added to this to form a dormant species. Polymer chains grow in a fashion similar to conventional polymerization by the addition of monomers to radicals. The polymerization is controlled by the reaction of CTA to the radicals and generation of dormant species. In a typical polymerization, a mixture of PEG acrylate/acylamide and functionalized L monomers along with S,S'-($\alpha,\alpha'$-dimethyl, $\alpha''$-dicarboxylic)trithiocarbonate as CTA agent and a radical initiator (e.g., azobis isovaleric acid) is used. Polymerization is initiated by the thermal cleavage by a radical initiator (e.g., azobis isovaleric acid but many others exist). Molecular weight of the polymer is controlled by the copolymerization conditions, i.e., the amount of each component used for the polymerization, copolymerization reactivity ratio of each component, temperature, ionic strength, pH, catalyst composition, catalyst concentration, catalyst reactivity, and solvent composition.

In Atom Transfer Radical Polymerization (ATRP), radicals or active species are generated through a reversible redox processes catalyzed by a transition metal complex ($Mt^n$-Y/Ligand, where Y may be another ligand or counter ion and M may be Cu, Fe, Ru or Ni) which undergoes one electron oxidation with concomitant abstraction of a halogen atom X from a dormant species R—X. This process occurs with a rate constant of activation, $K_{act}$ and deactivation, $K_{deact}$. Polymer chains grow by the addition of intermediate radicals to monomers similar to conventional radical polymerization with propagation rate constant $K_p$. In this invention Cu(I)Cl and 1,1,4,7,10,10-hexamethyl triethylene tetramine (HMTETA) is used catalyst. PEG acrylate or acrylamide and a functionalized L-monomer can be copolymerized using, for example, methyl-2-chloropropionate as initiator. Polymer molecular weight and composition is controlled by the copolymerization conditions; i.e., the amount of each component used for the polymerization, copolymerization reactivity ratio of each component, temperature, ionic strength, pH, catalyst composition, catalyst concentration, catalyst reactivity, and solvent composition.

In Free Radical Polymerization (FRP), radicals are generated by the homolytic cleavage of azobisisovaleric acid (radical initiator), and polymer chains grow by the addition of monomers to radicals. Polymerization and molecular weight is not controlled by FRP. In the present case PEG monomers (PEG acrylate/acrylamide) and functional monomers were copolymerized using azobisisovaleric acid as radical initiator to produce the chelation structure 10.

The chelation structure 10 of the present invention can be synthesized (using RAFT, ATRP, or FRP) via (1) bonding the chelators to a preformed backbone; or (2) copolymerization of the backbone, the polymer structures, and the chelators, as illustrated infra using PEG structures for the polymer structures.

2.1 Bonding the Chelators to a Preformed Backbone

Bonding the chelators to a preformed backbone comprises synthesizing a modified backbone (e.g., a pegylated backbone if the polymer structures comprise a PEG structure), followed by covalently bonding the at least one chelator to the corresponding bonding structures $B_L$ to form the chelation structure 10. The synthesized modified backbone comprises the backbone 12, the bonding structures $B_P$ and $B_L$ covalently bonded to the backbone at the corresponding monomeric backbone units, and the polymer structures covalently bonded to the corresponding bonding structure $B_P$.

Examples of bonding the chelators to a preformed backbone are next presented using RAFT, ATRP, and FRP.

2.1.1 Using RAFT to Bond the Chelators to a Preformed Backbone

In a first example, RAFT was used to bond an ICL670 chelator to a preformed backbone by synthesizing the backbone with a biodegradable bond, followed by covalent bonding of the ICL670 chelator to the synthesized backbone with a biodegradable bond.

To synthesize the backbone with a biodegradable bond, a mixture of 2-aminoethyl methacrylate hydrochloride (0.370 g), mPEG$_{350}$-acrylate (3.0 g), S,S'-($\alpha,\alpha'$-dimethyl, $\alpha''$-dicarboxylic)Trithiocarbonate (26.7 mg), Azobis isovaleric acid (4 mg) was dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer (mPEG-C-Amine) was dried in vacuum and analyzed by $^1$H NMR and GPC and titration. The Nuclear Magnetic Resonance (NMR) data regarding composition of the synthesized backbone are: $^1$H-NMR-CH$_3$-0.5-1.4 ppm, CH$_2$-1.5-2.3 ppm, CH$_2$—N 2.6-2.8 ppm, OCH$_3$ 3.35 ppm, —CH$_2$—O—CH$_2$-3.5-3.9 ppm, CH$_2$—O—CO 4.1 ppm. Gel permeation chromatography (GPC) data of backbone are: GPC-Mn-50500, Mw/Mn-1.1, wherein Mw represents the weight-average molecular weight and Mn represents the number-average molecular weight of a polymer.

To covalently bond the ICL670 chelator to the synthesized backbone via a biodegradable bond, PEG-C-Amine (0.70 g), ICL-670 (0.500 g) was dissolved in mixture of DMF (5 ml) and dichloromethane chloride (5 ml). Dicyclohexylcarbodiamide(DCC) (0.5 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for ICL-670 a molar ratio of ICL-670 to PEG units was calculated to be 1:4 in the polymer. The NMR data regarding composition of final product are: $^1$H-NMR-CH$_3$-0.5-1.4 ppm, CH$_2$-1.5-2.3 ppm, CH$_2$—N 2.6-2.8 ppm, OCH$_3$ 3.35 ppm, —CH$_2$—O—CH$_2$— 3.5-3.9 ppm CH$_2$—O—CO 4.1 ppm, ICL-670 peaks (7.1, 7.3, 7.7, 7.9 & 8.2 ppm).

Figure 6:
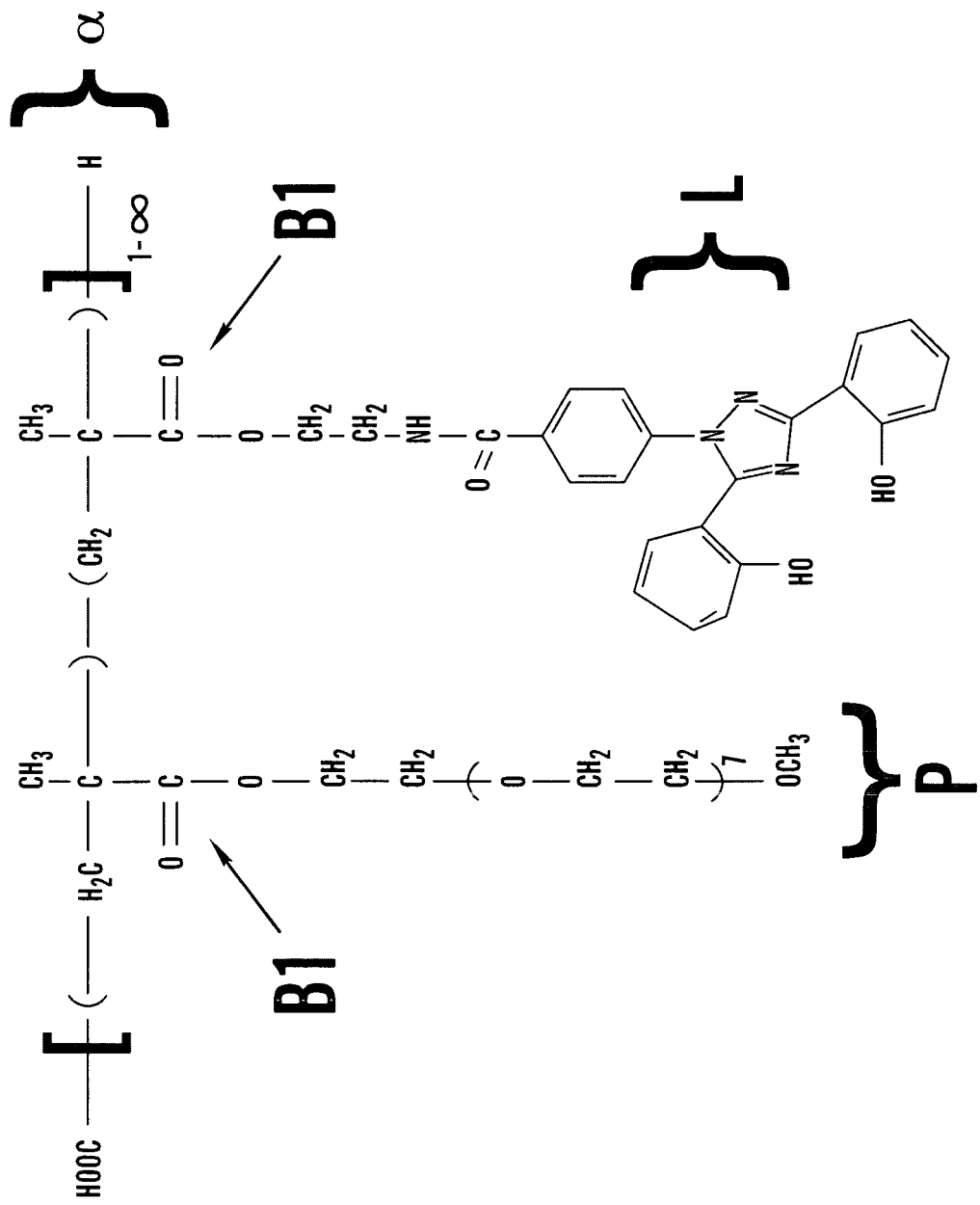
FIG. 6 depicts a synthesized chelation structure characterized by biodegradable bonds between the backbone and both the polymer and ICL-670 chelator subunits, in accordance with embodiments of the present invention.

The preceding process resulted in the synthesized chelation structure depicted in FIG. 6, in accordance with embodiments of the present invention. The chelation structure in FIG. 6 is characterized by biodegradable (B1) bonds between the acrylate/acrylamide backbone (α) and both the polymer (P) and the ICL-670 chelator (L) subunits.

In a second example, RAFT was used to bond an ICL670 chelator to a preformed backbone by synthesizing the backbone with a biodegradable bond, followed by covalent bonding of the ICL670 chelator to the synthesized backbone with a non-biodegradable bond.

To synthesize the backbone with a biodegradable bond, a mixture of N-(3-Aminopropyl)methacrylamide hydrochloride (0.399 g), mPEG$_{350}$-acrylate (3.0 g), S,S'-(α,α'-dimethyl, α"-dicarboxylic)Trithiocarbonate (28.6 mg), Azobis isovaleric acid (4.2 mg) was dissolved in dimethyl formamide (12 ml) and heated to 70° C. in an oil bath. Polymerization was continued for 24 h. Resulting polymer was precipitated in diethyl ether (150 ml). The precipitated polymer (mPEG-NC-Amine) was dissolved in methanol (5 ml) and again precipitated from diethyl ether (150 ml). The polymer was dried in vacuum and analyzed by $^1$H NMR and GPC and titration. The NMR data regarding composition of the synthesized backbone are: $^1$H-NMR-CH$_3$-0.5-1.4 ppm, CH$_2$-1.5-2.3 ppm, CH$_2$—N 2.7-3.1 ppm, OCH$_3$ 3.35 ppm, —CH$_2$—O—CH$_2$— 3.5-3.9 ppm, CH$_2$—O—CO 4.1 ppm. Gel permeation chromatography data of backbone are: GPC-Mn—55500, Mw/Mn—1.15.

To covalently bond the ICL670 chelator to the synthesized backbone via a non-biodegradable bond, PEG-NC-Amine (0.590 g), ICL-670 (0.280 g) was dissolved in mixture of DMF (5 ml) and dichloromethane (5 ml). Dicyclohexylcarbodiamide(DCC) (0.40 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for ICL-670 a molar ratio of ICL-670 to PEG units was calculated to be 1:16 in the polymer. The NMR data regarding composition of final product are: $^1$H-NMR-CH$_3$-0.5-1.4 ppm, CH$_2$— 1.5-2.3 ppm, CH$_2$—N 2.6-2.8 ppm, OCH$_3$ 3.35 ppm, —CH$_2$—O—CH$_2$— 3.5-3.9 ppm, CH$_2$—O—CO 4.1 ppm, ICL-670 peaks (broad peak from 7.1-8.6 ppm).

Figure 7:
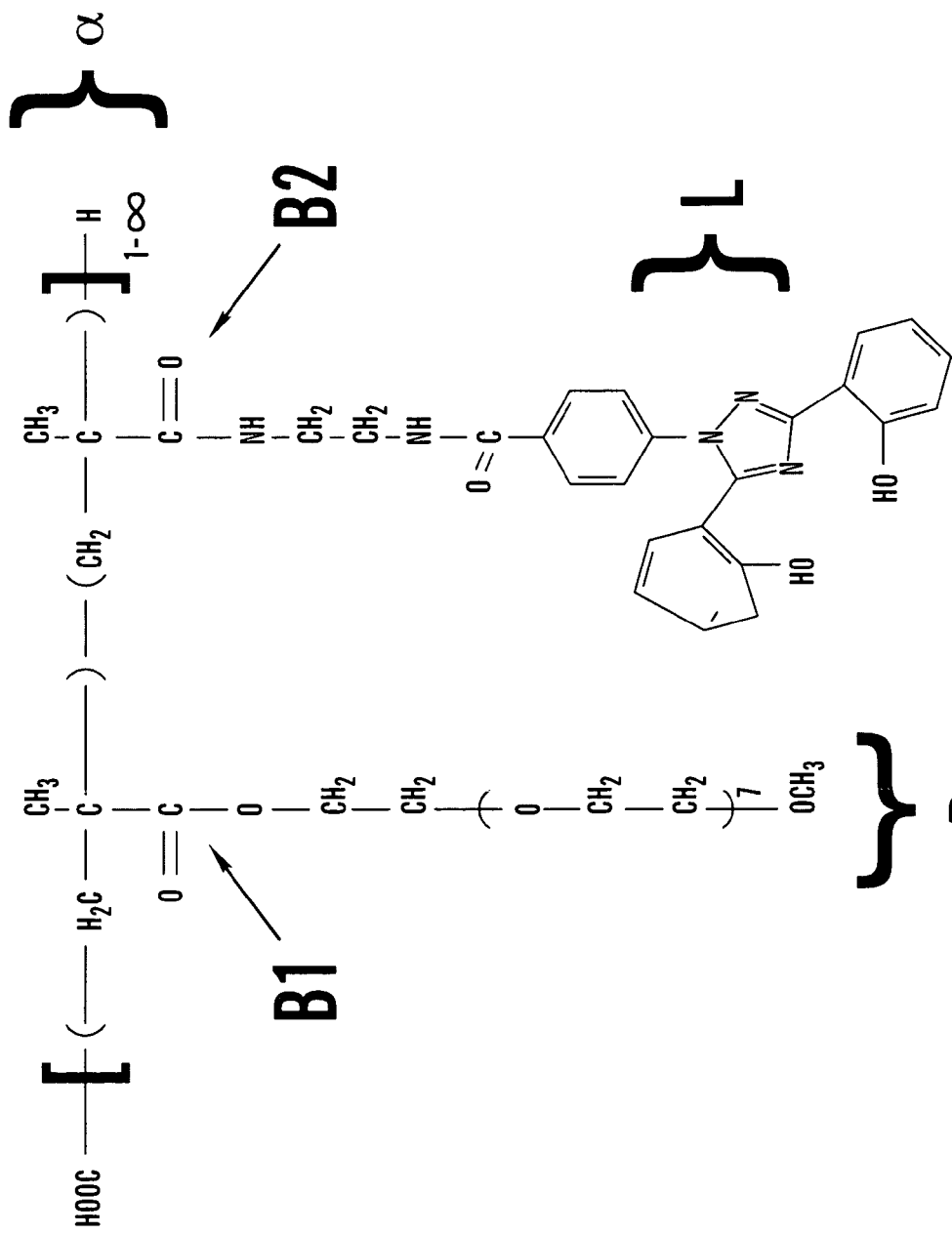
FIG. 7 depicts a synthesized chelation structure characterized by biodegradable bonds between the backbone and the polymer, and non-biodegradable bonds between the backbone and the ICL-670 chelator subunits, in accordance with embodiments of the present invention.

The preceding process resulted in the synthesized chelation structure depicted in FIG. 7, in accordance with embodiments of the present invention. The chelation structure in FIG. 7 is characterized by biodegradable (B1) bonds between the polymer (P) and the acrylate/acrylamide backbone (α), and a non-biodegradable (B2) bond between the backbone (α) and the ICL-670 chelator (L) subunits.

In a third example, RAFT was used to bond an HBED chelator to a preformed backbone by synthesizing the backbone with a biodegradable bond, followed by covalent bonding of the HBED chelator to the synthesized backbone with a non-biodegradable bond.

To synthesize the backbone with a biodegradable bond, a mixture of acrylic acid (0.300 g), MPEG$_{350}$-acrylate (3.0 g), S,S'-(α, α'-dimethyl, α"-dicarboxylic)Trithiocarbonate (28.6 mg), Azobis isovaleric acid (4.2 mg) were dissolved in dimethyl formamide (12 ml) and heated to 70° C. in an oil bath. Polymerization was continued for 24 h. The resulting polymer (mPEG-NC-Acid) was precipitated in diethyl ether (150 ml). The precipitated polymer was dissolved in methanol (5 ml) and again precipitated from diethyl ether (150 ml).

To covalently bond the HBED chelator to the synthesized backbone via a non-biodegradable bond, PEG-NC-Acid (0.650 g) and carboxyl protected amine functionalized HBED (HBED-Amine) (0.300 g) were dissolved in mixture of DMF (5 ml) and dichloromethane (5 ml). Dicyclohexylcarbodiamide (DCC) (0.40 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for HBED, a molar ratio of HBED to PEG units was calculated to be 1:12 in the polymer.

2.1.2 Using ATRP To Bond the Chelators to a Preformed Backbone

In a first example, ATRP was used to bond an ICL670 chelator to a preformed backbone by synthesizing the backbone with a biodegradable bond, followed by covalent bonding of the ICL670 chelators to the synthesized backbone with a nonbiodegradable bond.

To synthesize the backbone with a biodegradable bond, 2-aminoethyl methacrylate hydrochloride (0.4 g), MPEG$_{350}$-acrylate (3.0 g), 1,1,4,7,10,10-hexamethyl triethylene tetramine (Aldrich, 97%) (HMTETA), CuCl and CuCl$_2$ were used. Methyl 2-chloropropionate was used as initiator. All the reagents were dissolved in dimethyl formamide (12 ml) and the reaction was conducted at 50° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum.

To covalently bond the ICL670 chelator to the synthesized backbone via a nonbiodegradable bond, PEG-C-Amine (A-P) (0.80 g) and ICL-670 (0.600 g) were dissolved in mixture of DMF (5 ml) and dichloromethane chloride (5 ml). Dicyclohexylcarbodiamide (DCC) (0.5 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for ICL-670, a molar ratio of ICL-670 to PEG units was calculated to be 1:4 in the polymer.

In a second example, ATRP was used to bond an HBED chelator to a preformed backbone by synthesizing the backbone with a biodegradable bond, followed by covalent bonding of the HBED chelator to the synthesized backbone with a nonbiodegradable bond.

To synthesize the backbone with a biodegradable bond, a mixture of acrylic acid sodium salt (0.350 g), MPEG$_{350}$-acrylamide (3.0 g), 1,1,4,7,10,10-hexamethyl triethylene tetramine (Aldrich, 97%) (HMTETA), CuCl and CuCl$_2$ were dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum.

To covalently bond the HBED chelator to the synthesized backbone via a nonbiodegradable bond, MPEG- -Acid (A-P) (1.0 g), carboxyl protected amine functionalized HBED (HBED-Amine) (0.500 g) were dissolved in mixture of DMF (10 ml) and dichloromethane (5 ml). Dicyclohexylcarbodiamide (DCC) (0.80 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for HBED, a molar ratio of HBED to PEG units was calculated to be 1:10 in the polymer.

2.1.3 Using FRP to Bond the Chelators to a Preformed Backbone

In a first example, FRP was used to bond an ICL670 chelator to a preformed backbone by synthesizing the backbone with a biodegradable bond, followed by covalent bonding of the ICL670 chelators to the synthesized backbone with a biodegradable bond.

To synthesize the backbone with a biodegradable bond, a mixture of 2-aminoethyl methacrylate hydrochloride (0.4 g), mPEG$_{350}$-acrylate (3.0 g) and Azobis isovaleric acid (4 mg) were dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum.

To covalently bond the ICL670 chelator to the synthesized backbone via a biodegradable bond, PEG-C-Amine (A-P) (0.70 g) and ICL-670 (0.500 g) were dissolved in mixture of DMF (5 ml) and dichloromethane chloride (5 ml). Dicyclohexylcarbodiamide(DCC) (0.5 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for ICL-670, a molar ratio of ICL-670 to PEG units was calculated to be 1:4 in the polymer.

In a second example, FRP was used to bond an HBED chelator to a preformed backbone by synthesizing the backbone with a biodegradable bond, followed by covalent bonding of the HBED chelators to the synthesized backbone with a nonbiodegradable bond.

To synthesize the backbone with a biodegradable bond, a mixture of acrylic acid (0.300 g), MPEG$_{350}$-acrylamide (3.0 g) and Azobis isovaleric acid were dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum.

To covalently bond the HBED chelator to the synthesized backbone via a nonbiodegradable bond, MPEG- -Acid (A-P) (1.0 g) and carboxyl protected amine functionalized HBED (HBED-Amine) (0.600 g) were dissolved in mixture of DMF (10 ml) and dichloromethane (5 ml). Dicyclohexylcarbodiamide (DCC) (0.80 g) dissolved in 5 ml of dichloromethane chloride was added slowly at 0° C. to the polymer mixture and stirred for 24 h at room temperature. The product was precipitated twice from diethyl ether and characterized by $^1$HNMR and UV-VIS spectroscopy. From the intensity of peaks for HBED, a molar ratio of HBED to PEG units was calculated to be 1:8 in the polymer.

2.2 Copolymerization of the Backbone the PEG Structures, and the Chelators

Figure 8:
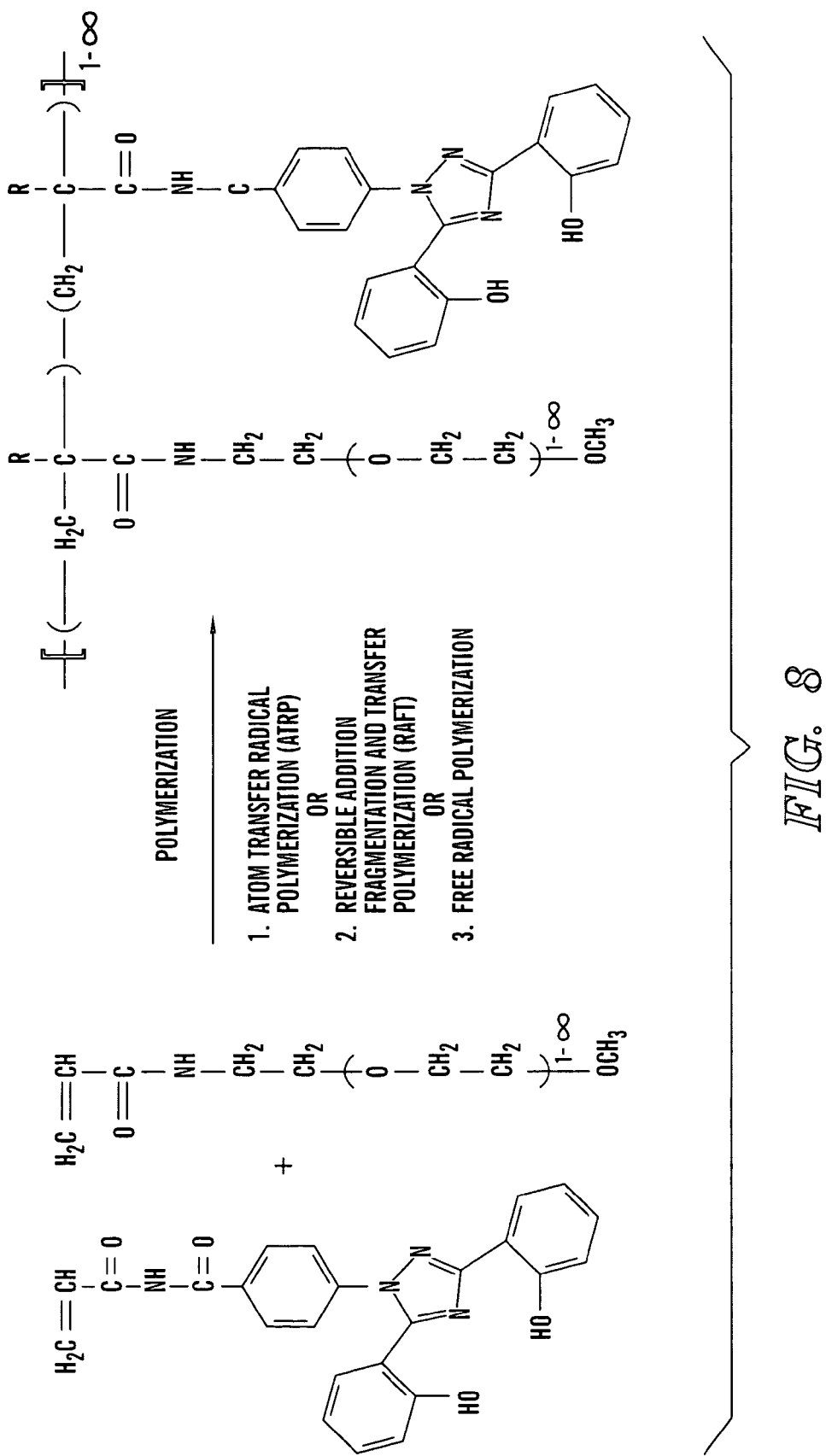
FIG. 8 depicts a general single step synthesis of a chelation structure using an ICL-670 chelator, in accordance with embodiments of the present invention.
Figure 9:
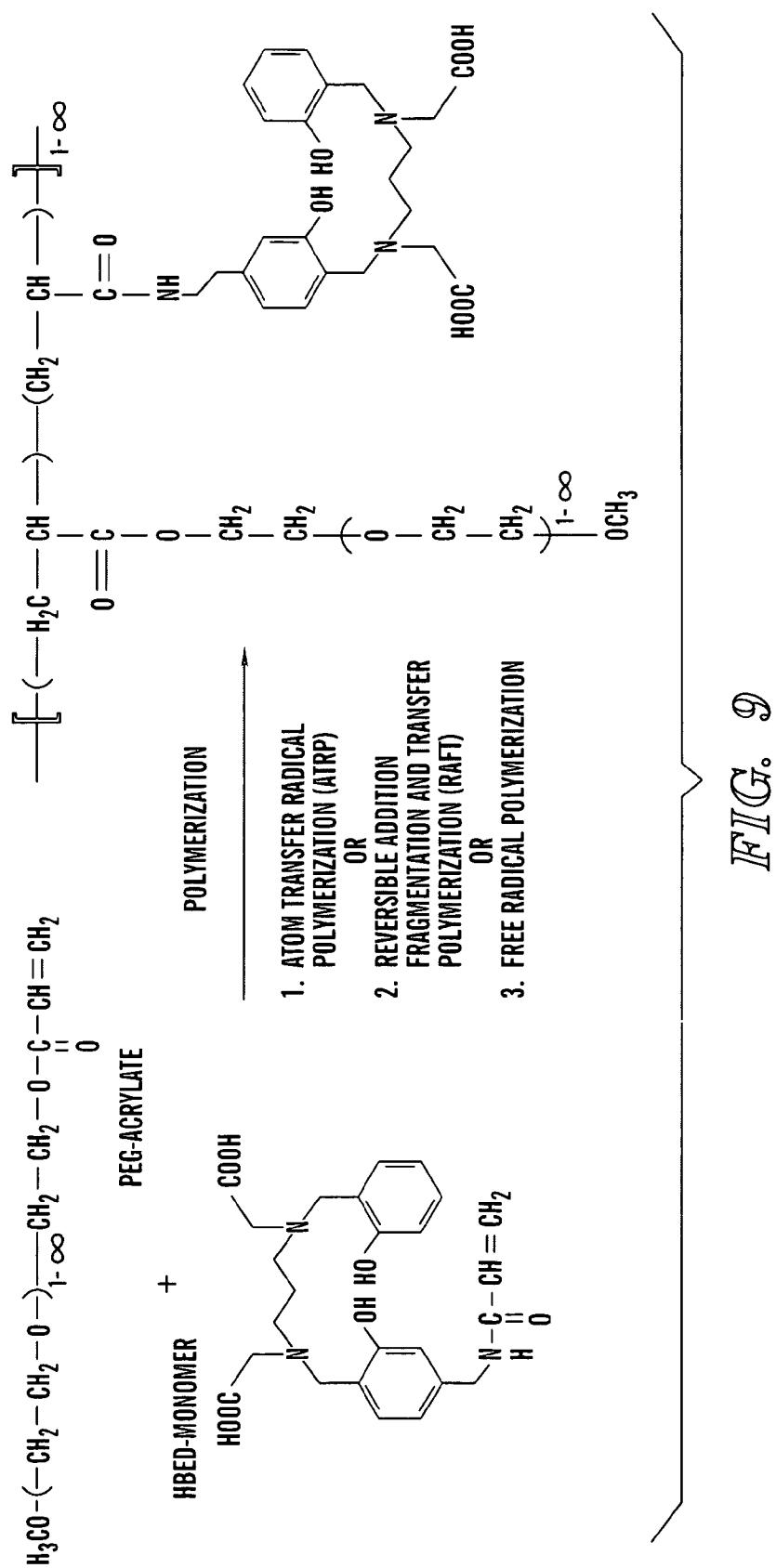
FIG. 9 depicts a general single step synthesis of a chelation structure using an HBED chelator, in accordance with embodiments of the present invention.
Figure 10:
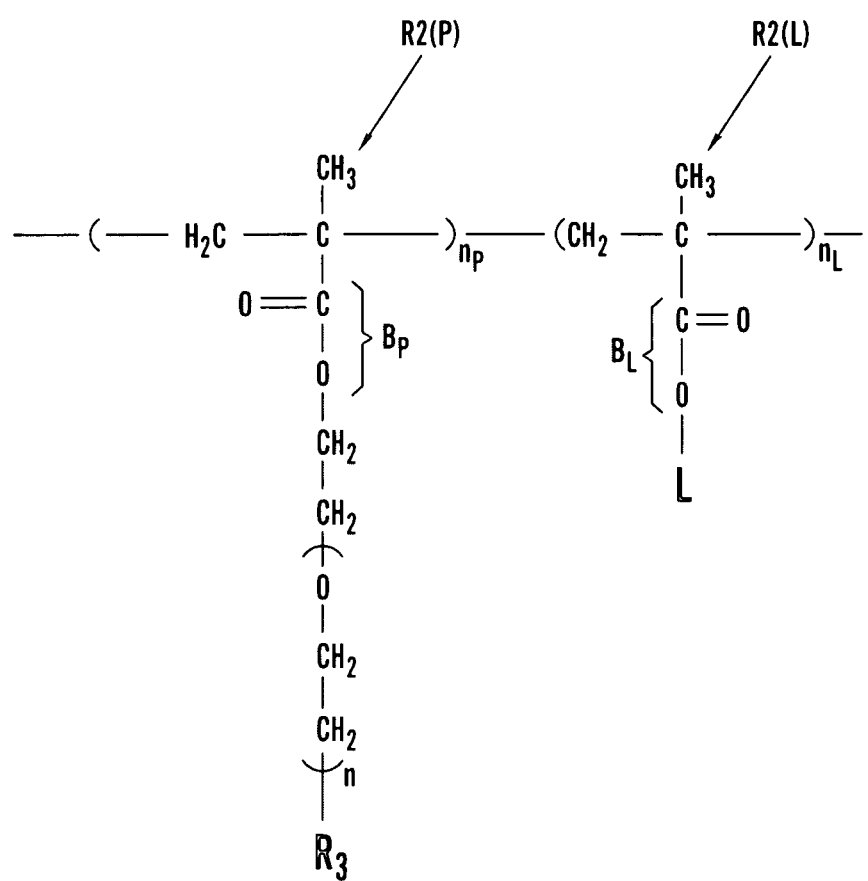
FIGS. 10-19 depict chelation structures showing different combinations of monomeric backbone units and biodegradable/non-biodegradable linkages between the backbone and both the poly(ethylene glycol) (PEG) side chains and the chelator side chains, in accordance with embodiments of the present invention.
Figure 11:
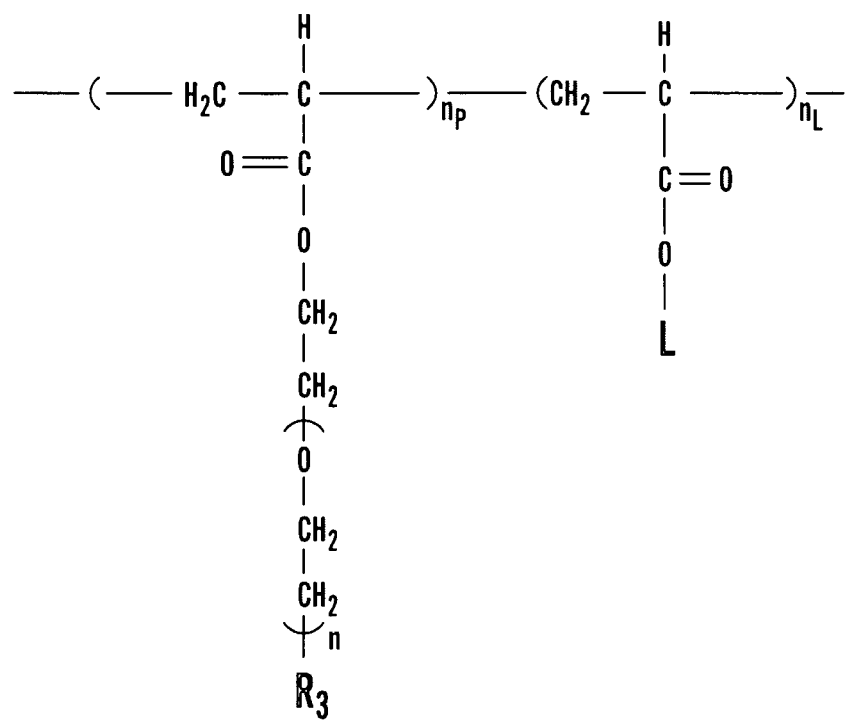
Figure 12:
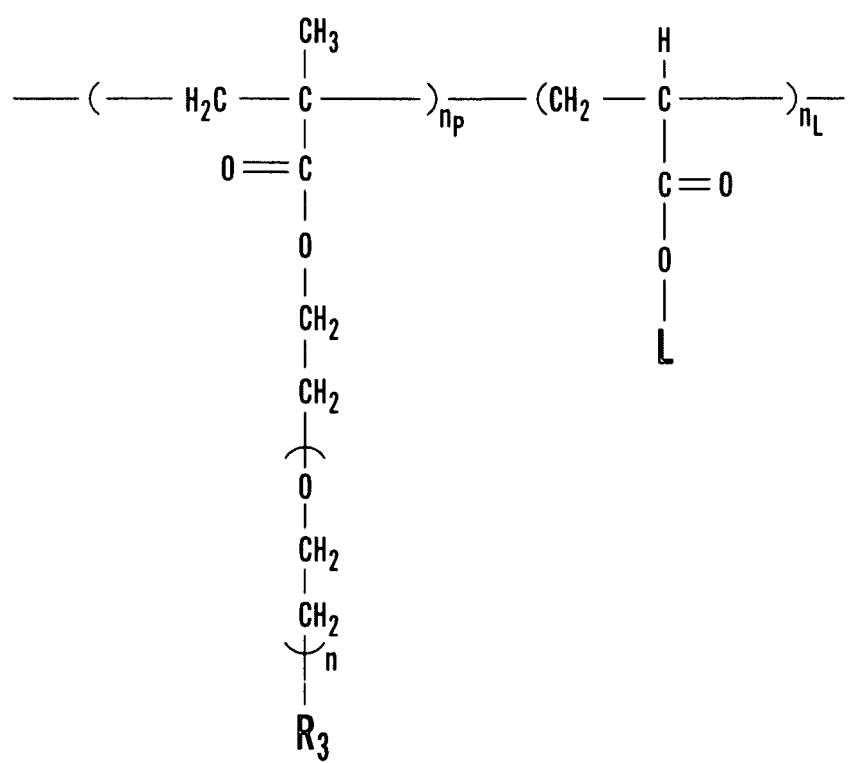
Figure 13:
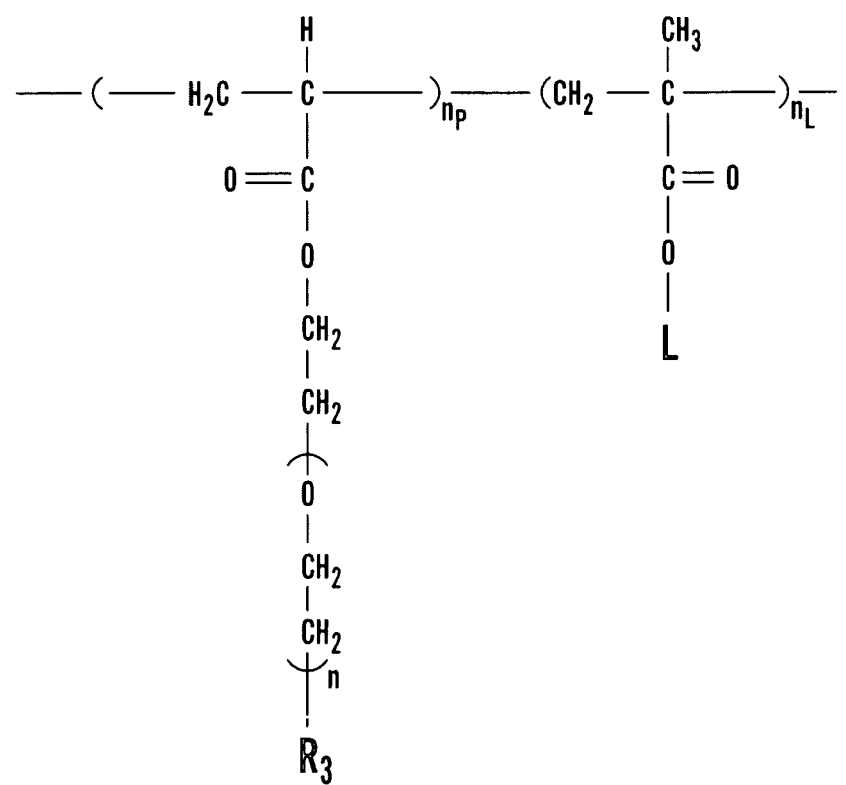
Figure 14:
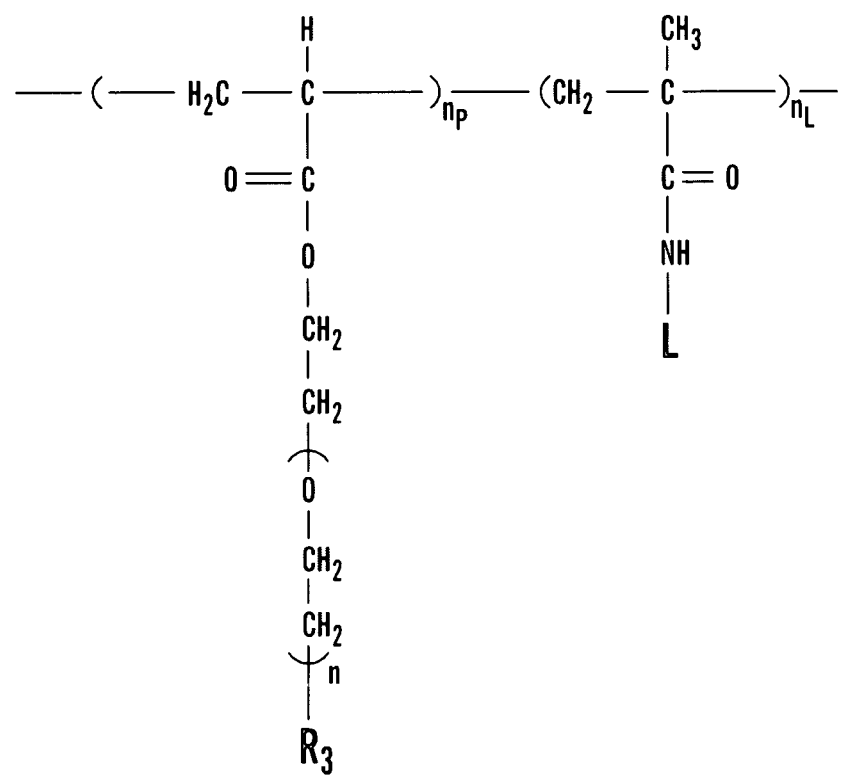
Figure 15:
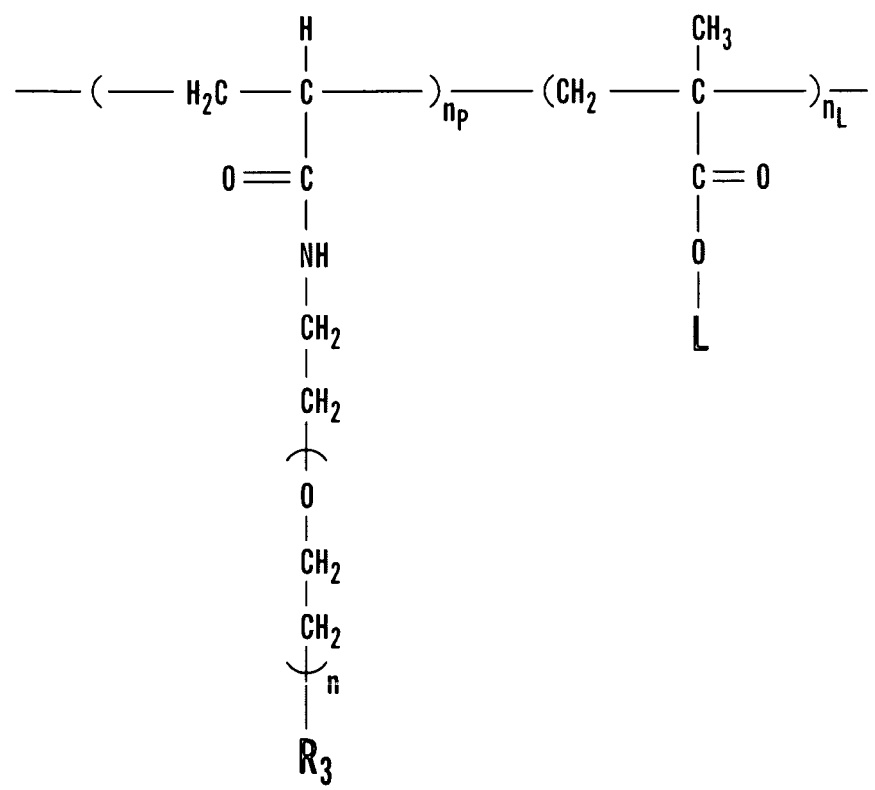
Figure 16:
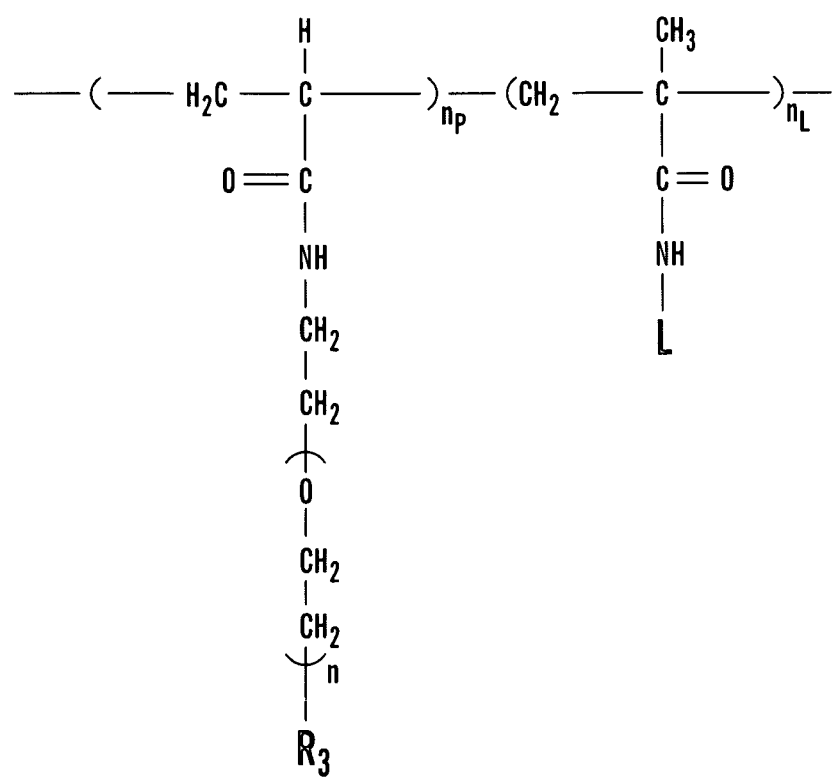
Figure 17:
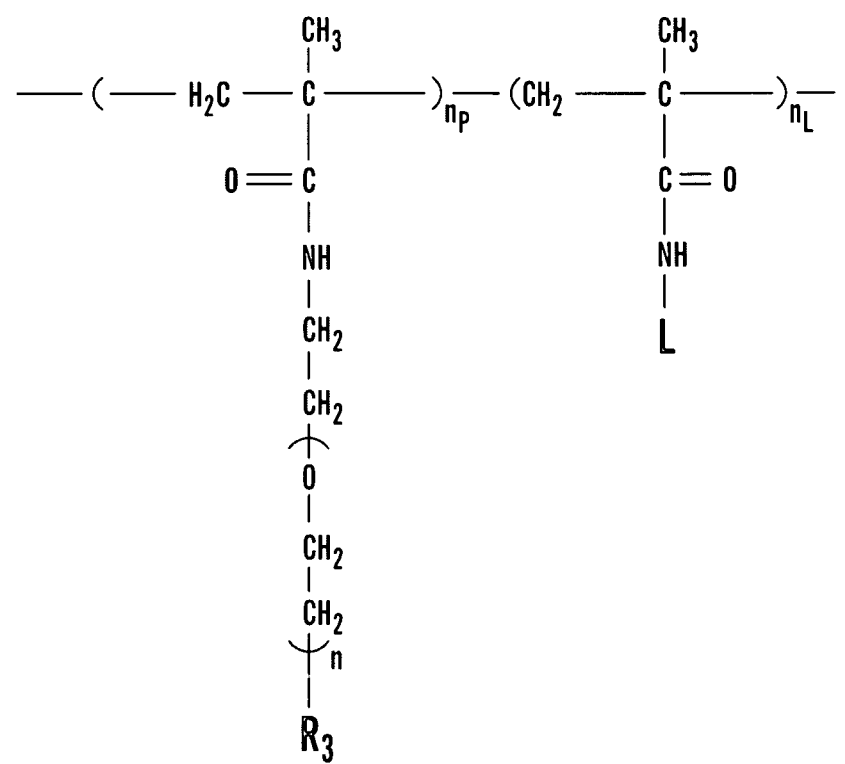
Figure 18:
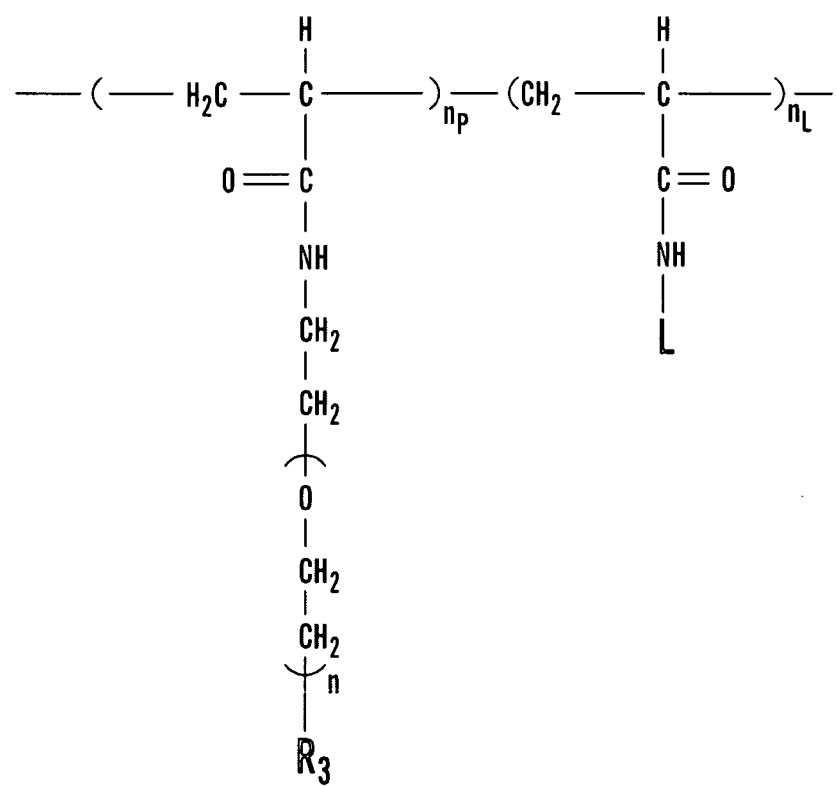
Figure 19:
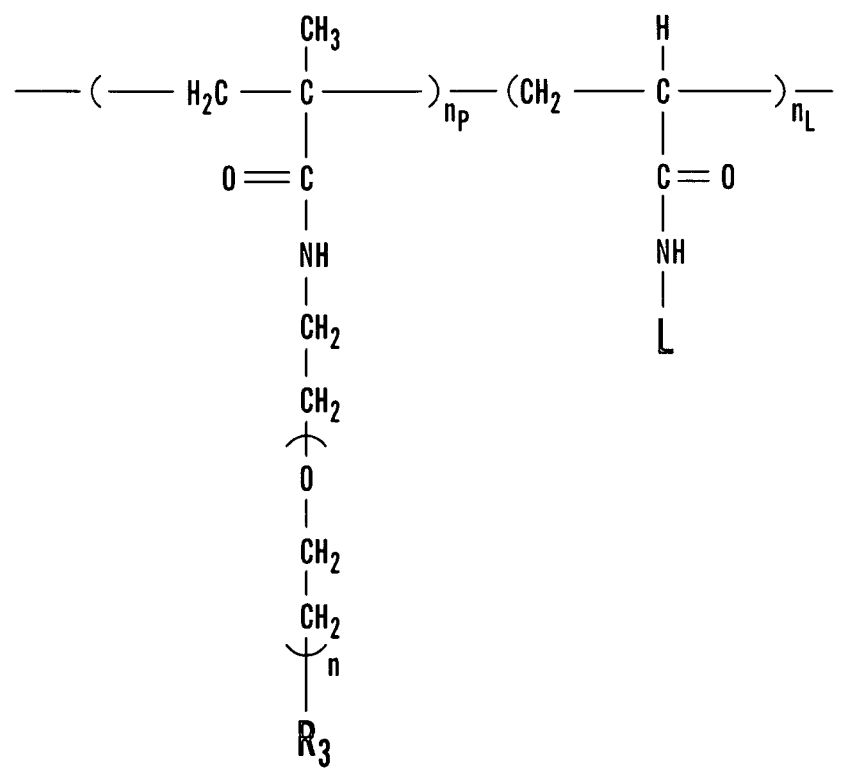

The copolymerization methodology involves a single step synthesis utilizing monomeric units of (P), (L). (P) and (L) are derivatized to incorporate the backbone subunit associated with monomeric units A1 and A2 of FIG. 1. A1 and A2 react to form a covalent A1-A2 bond forming the backbone macromolecule. Multiple means of synthesis can be used. These include RAFT, ATRP and FRT. FIGS. 8 and 9 show the general scheme of synthesis for ICL-670 (FIG. 8) and HBED (FIG. 9) chelation structures of the present invention.

FIG. 8 depicts a general single step synthesis of a chelation structure using an ICL-670 chelator, in accordance with embodiments of the present invention. The example shown utilizes ICL-670 (L) and a PEG derivative [(P); methoxypoly (ethylene glycol)]. Chelator (L) and PEG structure (P) are covalently bound to the A1 and A2 subunits via non-biodegradable bonds (B2) in this example of synthesis.

FIG. 9 depicts a general single step synthesis of a chelation structure using an HBED chelator, in accordance with embodiments of the present invention. The example shown utilizes HBED (L) and a PEG derivative [(P); methoxypoly (ethylene glycol)]. Chelator (L) and PEG structure (P) are covalently bound to the A1 and A2 subunits of the backbone. (P) is bound via a biodegradable (B1) bond while (L) is covalently bound via a non-biodegradable bond (B2) in this example of synthesis.

Examples of generating the chelator structure by copolymerization are next presented using RAFT, ATRP, and FRP.

2.2.1 Using RAFT To Copolymerize the Chelation Structure

In a first example, RAFT was used to copolymerize the chelation structure, using an ICL-670 chelator. ICL-670 acrylamide (0.4 g), MPEG$_{350}$-acrylate (3.0 g), S,S'-($\alpha$, $\alpha$'-dimethyl, $\alpha$"-dicarboxylic)Trithiocarbonate (26.7 mg), Azobis isovaleric acid (4 mg) was dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum and analyzed by $^1$H NMR and GPC and titration.

In a second example, RAFT was used to copolymerize the chelation structure, using an HBED chelator. HBED-acrylamide (0.5 g), MPEG$_{350}$-acrylate (3.0 g), S,S'-($\alpha$, $\alpha$'-dimethyl, $\alpha$"-dicarboxylic)Trithiocarbonate (26.7 mg), Azobis isovaleric acid (4 mg) was dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum and analyzed by $^1$H NMR and GPC and titration.

2.2.2 Using ATRP to Copolymerize the Chelation Structure

In a first example, ATRP was used to copolymerize the chelation structure, using an ICL-670 chelator. ICL-670 acrylamide (0.4 g), MPEG$_{350}$-acrylate (3.0 g), 1,1,4,7,10,10-hexamethyl triethylene tetramine (Aldrich, 97%) (HMTETA), CuCl, CuCl$_2$ were used. Methyl 2-chloropropionate was used as initiator. All the reagents were dissolved in dimethyl formamide (12 ml) and reaction was conducted at 50° C. in an oil bath. Polymerization was continued for 24 h. Resulting polymer was precipitated in diethyl ether (150 ml). The precipitated polymer was dissolved in methanol (5 ml) and again precipitated from diethyl ether (150 ml). The polymer was dried in vacuum and analyzed by $^1$H NMR and GPC and titration.

In a second example, ATRP was used to copolymerize the chelation structure, using an HBED chelator. HBED-acrylamide (0.5 g), MPEG$_{350}$-acrylate (3.0 g), 1,1,4,7,10,10-hexamethyl triethylene tetramine (Aldrich, 97%) (HMTETA), CuCl, CuCl$_2$ were used. Methyl 2-chloropropionate was used as initiator. All the reagents were dissolved in dimethyl formamide (12 ml) and reaction was conducted at 50° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum and analyzed by $^1$H NMR and GPC and titration.

2.2.3 Using FRP to Copolymerize the Chelation Structure

In a first example, FRP was used to copolymerize the chelation structure, using an ICL-670 chelator. ICL-670 acrylamide (0.4 g), MPEG$_{350}$-acrylate (3.0 g), Azobis isovaleric acid (4 mg) was dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum and analyzed by $^1$H NMR and GPC and titration.

In a second example, FRP was used to copolymerize the chelation structure, using an HBED chelator. HBED-acrylamide (0.5 g), MPEG$_{350}$-acrylate (3.0 g), Azobis isovaleric acid (4 mg) was dissolved in dimethyl formamide (12 ml) and heated to 70° C. in an oil bath. Polymerization was continued for 24 h. The resulting polymer was precipitated in diethyl ether (150 ml). The precipitated polymer was dissolved in methanol (5 ml) and again precipitated from diethyl ether (150 ml). The polymer was dried in vacuum and analyzed by $^1$H NMR and GPC and titration.

2.3 Controlling the Chelation Structure

The distribution of biodegradable bond B1, non-biodegradable bond B2, PEG structure P, and chelator L along the backbone in the chelation structure of the present invention is dependent upon the synthesis route. However, in all routes of synthesis, the distribution of P and L as well as B1 and B2 along the backbone is controlled by the copolymerization conditions; i.e., the amount of each component used for the polymerization, copolymerization reactivity ratio of each component, temperature, ionic strength, pH, catalyst composition, catalyst concentration, catalyst reactivity, and solvent composition. Control of the copolymerization conditions is next illustrated for the embodiments of using a preformed backbone and of using copolymerization of individual monomeric components.

2.3.1. Using Preformed Backbone

P is binded to a preformed backbone of variable length. The backbone contains the B1 and B2 reactive binding sites to which P reacts. By manipulating the treatment conditions of the backbone, the ratio of B1 to B2 on the backbone can be controlled. After binding P, L is then added at the desired concentrations and the added L reacts with remaining B1 or B2 sites. The backbone can have: only B1 sites; only B2 sites; or a mixture of B1 and B2 sites. Thus pre-modification of P dictates if the P binds to a B1 site, a $B_2$ site, or both a B1 site and a B2 site. Similarly, pre-modification of L dictates if the L binds to a B1 site, a B2 site, or both a B1 site and a B2 site.

2.3.2 Using Copolymerization of Individual Monomeric Components

Using copolymerization of individual monomeric components, no backbone is initially present but is formed by the reaction of modified P and L monomers. The final size of generated backbone is governed by the number of L and P linked together by the backbone. B1 or B2 are present on the P or L subunits. For both P and L, there may be: all B1; all B2; or a combination of B1 and B2. The combination of B1 and B2 may be achieved by mixing B1 and B2 modified monomers. Furthermore, P could be linked entirely to B1, B2, or a mixture of B1 and B2, whereas L could be linked entirely to B1, B2, or a mixture of B1 and B2. Thus a chelator can be designed where, for example, all P modules are bound by a B1 linkage to facilitate biological clearance, while all L modules are bound by a B2 linkage to the stable backbone for eventual clearance and to prevent metal mediated injury.

3. Validation of Chelation Structure Functionality

Current low molecular weight metal chelators under development for clinical usage are beset by problems on insolubility in aqueous solutions such as water and physiological plasma. The chelation structure of the present invention, however, is not best by such solubility problems, as illustrated in FIG. 20.

Figure 20A:
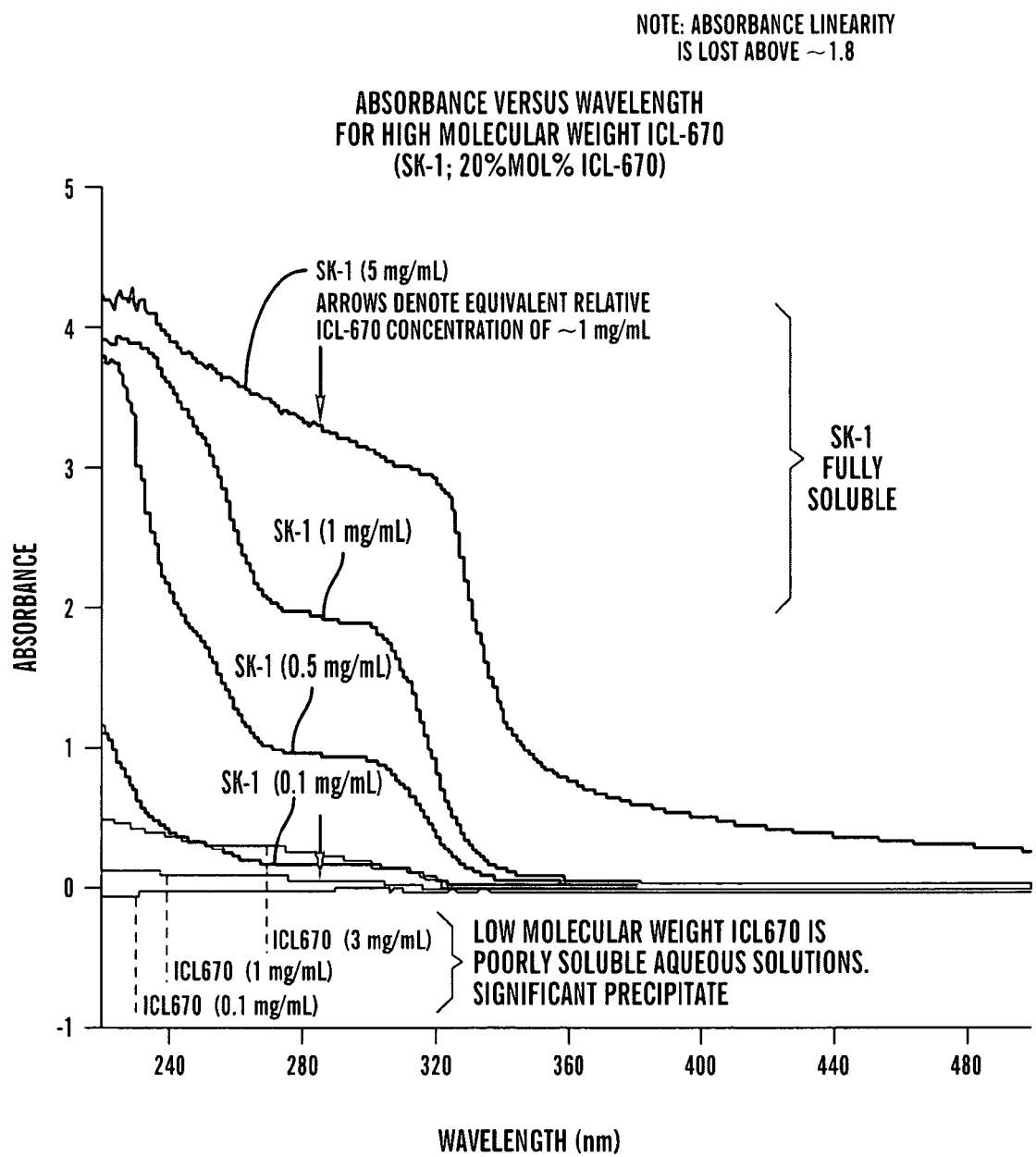
FIGS. 20A and 20B are plots of absorbance of radiation versus wavelength of the radiation in water for various chelators dissolved in the water, in accordance with embodiments of the present invention.
Figure 20B:
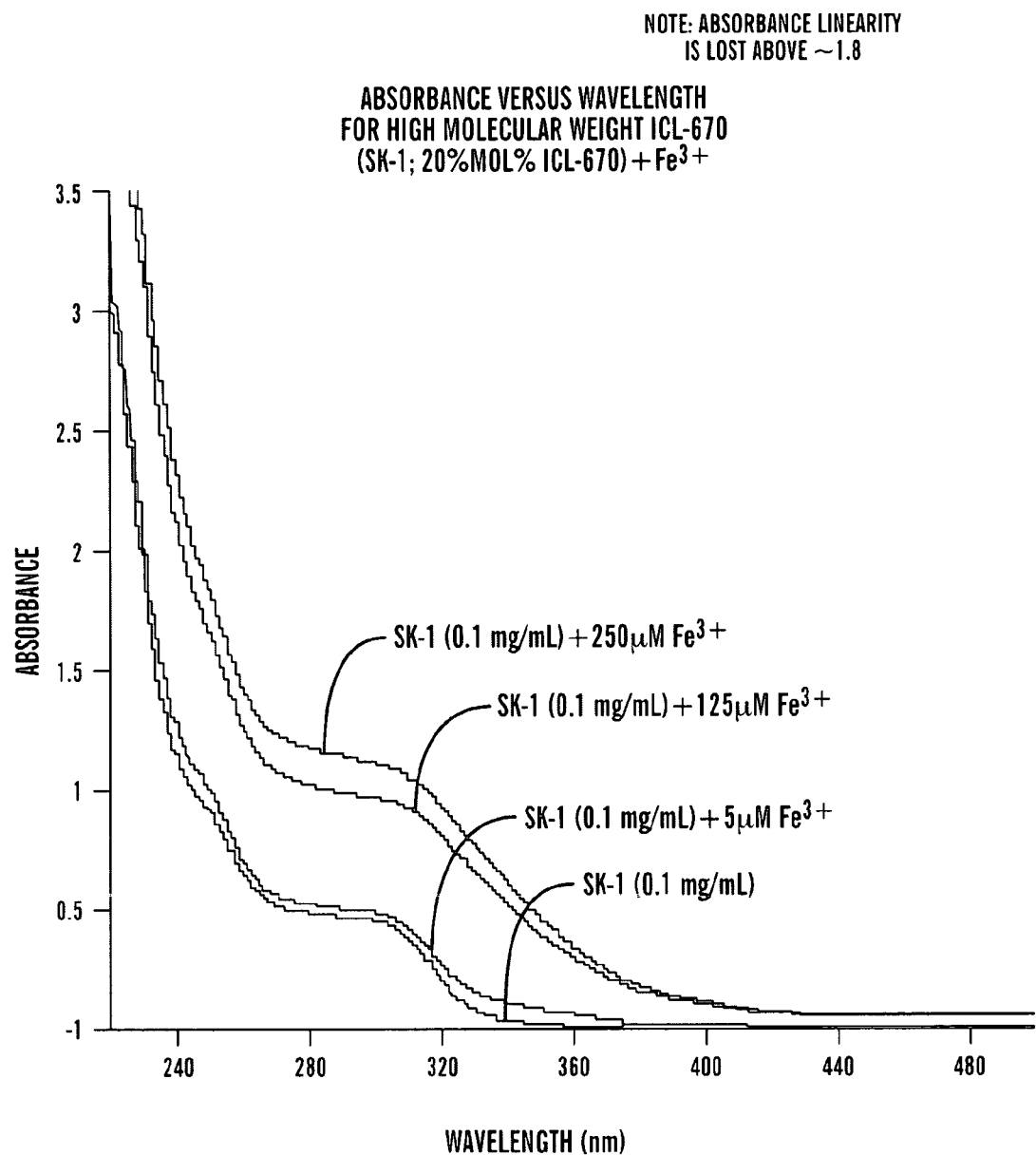

FIGS. 20A and 20B are plots of absorbance of radiation in water versus wavelength of the radiation, for low molecular weight ICL670 (3 mg/ml) and the chelation structure of the present invention (denoted as HMW) dissolved in the water, in accordance with embodiments of the present invention. FIG. 20A shows plots for the chelator ICL-670 and the chelation structure SK-1 (i.e., the high molecular weight (HWM) chelation structure of the present invention using the chelator ICL-670). FIG. 20B shows plots for SK-1 plus $Fe^{3+}$. The measured absorbance increases with increasing concentration of the chelators/chelation structures dissolved in the water and is thus a measure of the solubility of the chelators/chelation structures in the water.

As shown, preparation of the HWM chelation structure of the present invention using ICL-670 dramatically improves its solubility in water (shown) and plasma (not shown). In addition as denoted by the arrow in FIG. 20A, the equivalent ICL-670 content in SK-1 (5 v mg/mL) in comparison with the 1 mg/mL for ICL-670 shows vastly improved solubility. Consequent to its improved solubility characteristics, improved therapeutic dosages can be achieved by the chelation structure of the present invention. The improved solubility of the IC-670 in the chelation structure of the present invention is dependent upon both the monomeric backbone units ($A_1$, $A_2$, . . . , $A_N$) and the PEG structures P.

FIG. 20A shows that the low molecular weight ICL670 is insoluble in water with large amounts of precipitates (ppt.) present. In contrast, the High Molecular Weight (HMW) form of ICL-670 of the present invention demonstrates full solubility in water at high concentrations. The HMW-ICL-670 used was 20% (by weight) ICL-670. At no concentration were precipitates noted in the samples used for analysis for the HMW-ICL-670. Linearity is lost at absorbance values greater than 2, thought the improved solubility is further noted by the tail located between wavelengths of 360-640 nm for the highest concentrations of the HMW-ICL670.

FIG. 20B shows the spectral shift of SK-1 as the SK-1 binds iron demonstrating that the iron chelation ability of ICL-670 is not lost upon covalent linkage to the SK-1 backbone.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A chelation structure, comprising:
a backbone structured as $R_0$–$(A_1$-$A_2$- . . . -$A_N$)–$R_1$, wherein $N \geq 3$, wherein $A_1$-$A_2$- . . . -$A_N$ is a linearly connected sequence of N monomeric backbone units, wherein for A representing one of $A_1, A_2, \ldots A_N$, -A- is structured as

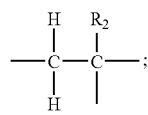

bonding structures (B) each covalently bonded to a corresponding monomeric backbone unit A in a form of A-B, wherein A-B is structured as

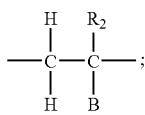

at least one water-soluble polymer structure (P), wherein each polymer structure P is covalently coupled to the corresponding monomeric backbone unit A by a corresponding bonding structure ($B_P$) of the bonding structures (B) according to A-$B_P$-P such that $B_P$-P is a polymer side chain covalently bonded to the backbone at A, and wherein $B_P$ is independently biodegradable or non-biodegradable for each polymer side chain $B_P$-P;

at least one chelator (L), wherein each chelator L is covalently coupled to the corresponding monomeric backbone unit A by a corresponding bonding structure ($B_L$) of the bonding structures (B) such that $B_L$-L is a chelator side chain covalently bonded to the backbone at A, and wherein $B_L$ is independently biodegradable or non-biodegradable for each P chelator side chain $B_L$-L;

wherein $R_0$ and $R_1$ are independently selected from the group consisting of a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, and an epoxide group;

wherein for each monomeric unit, $R_2$ is independently selected from the group consisting of hydrogen group, an alkyl group, a benzyl group, and an aryl group;

wherein for each polymer side chain, P is independently selected from the group consisting of a poly(ethylene glycol) (PEG) structure, a poly(propylene glycol) group, a poly(acrylamide) group, a N-substituted polyacrylamides group, a carbohydrate polymer group, an oligosaccharide group, a polyvinyl alcohol group, a polyglycerol group, and a polyvinylpyrolidone group; and wherein the at least one polymer structure is a plurality of polymer structures;

wherein for each chelator side chain, the chelator L has a log stability constant $K_L$ no less than 15 for binding a substance selected from the group consisting of at least one metal, heme, and a combination thereof;

wherein the plurality of polymer structures comprises the PEG structure having a form of $R_4$-$(R_5)_m$-$R_3$, wherein $R_4$ is independently $CH_2$-$CH_2$ or a modified $CH_2$-$CH_2$, wherein $R_5$ is independently O-$CH_2$-$CH_2$ or a substituted O-$CH_2$-$CH_2$, wherein m is a positive integer, and wherein $R_3$ is selected from the group consisting of a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, an epoxide group, a halide group, an amino acid group, a carbohydrate group, and a peptide group.

2. The chelation structure of claim 1, wherein a bonding structure ($B_1$) of all of said bonding structures $B_P$ and $B_L$ is biodegradable.

3. The chelation structure of claim 2, wherein the bonding structure $B_1$ is selected from the group consisting of an ester group, a substituted esters group, a disulfide group, a substituted disulfide group, an acetal group, a ketal group, a glycoside group, an anhydride group, a peptide group, and a urethane group.

4. The chelation structure of claim 1, wherein a bonding structure ($B_2$) of all of said bonding structures $B_P$ and $B_L$ is non-biodegradable.

5. The chelation structure of claim 4, wherein the bonding structure $B_2$ is selected from the group consisting of a N-substituted amide group, a benzyl group, an aryl group, an alkyl group, and an ether group.

6. The chelation structure of claim 1, wherein $R_4$ is $CH_2$-$CH_2$.

7. The chelation structure of claim 1, wherein $R_4$ is the modified $CH_2$-$CH_2$.

8. The chelation structure of claim 1, wherein $R_5$ is O-$CH_2$-$CH_2$.

9. The chelation structure of claim 1, wherein $R_5$ is the substituted O-$CH_2$-$CH_2$.

10. The chelation structure of claim 1, wherein $R_3$ is OH.

11. A chelation structure, comprising:
a backbone structured as $R_0$-($A_1$-$A_2$-....-$A_N$)-$R_1$, wherein $N \geq 3$, wherein $A_1$-$A_2$-....-$A_N$ is a linearly connected sequence of N monomeric backbone units, wherein for A representing one of $A_1, A_2, \ldots A_N$, -A- is structured as

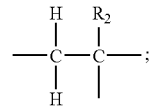

bonding structures (B) each covalently bonded to a corresponding monomeric backbone unit A in a form of A-B, wherein A-B is structured as

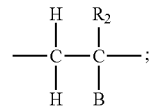

at least one water-soluble polymer structure (P), wherein each polymer structure P is covalently coupled to the corresponding monomeric backbone unit A by a corresponding bonding structure ($B_P$) of the bonding structures (B) according to A-$B_P$-P such that $B_P$-P is a polymer side chain covalently bonded to the backbone at A, and wherein $B_P$ is independently biodegradable or non-biodegradable for each polymer side chain $B_P$-P;

at least one chelator (L), wherein each chelator L is covalently coupled to the corresponding monomeric backbone unit A by a corresponding bonding structure ($B_L$) of the bonding structures (B) such that $B_L$-L is a chelator side chain covalently bonded to the backbone at A, and wherein $B_L$ is independently biodegradable or non-biodegradable for each P chelator side chain $B_L$-L;

wherein $R_0$ and $R_1$ are independently selected from the group consisting of a hydrogen group, an alkyl group, an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, and an epoxide group;

wherein for each monomeric unit, $R_2$ is independently selected from the group consisting of hydrogen group, an alkyl group, a benzyl group, and an aryl group;

wherein for each polymer side chain, P is independently selected from the group consisting of a poly(ethylene glycol) (PEG) structure, a poly(propylene glycol) group, a poly(acrylamide) group, a N-substituted polyacrylamides group, a carbohydrate polymer group, an oligosaccharide group, a polyvinyl alcohol group, a polyglycerol group, and a polyvinylpyrolidone group; and wherein the at least one polymer structure is a plurality of polymer structures;

wherein for each chelator side chain, the chelator L has a log stability constant $K_L$ no less than 15 for binding a substance selected from the group consisting of at least one metal, heme, and a combination thereof;

wherein the at least one chelator comprises at least two different chelators.

12. The chelation structure of claim 11, wherein at least one monomeric backbone unit of monomeric backbone units $A_1$, $A_2$, ... $A_N$ does not have a side chain attached thereto.

13. The chelation structure of claim 11, wherein a polymer structure of the plurality of polymer structures is a linear polymer structure.

14. The chelation structure of claim 11, wherein a polymer structure of the plurality of polymer structures is a branched polymer structure.

15. The chelation structure of claim 11, wherein said polymer structures and said chelators are distributed with respect to each other along the backbone in accordance with a predetermined pattern.

16. The chelation structure of claim 11, wherein said polymer structures and said chelators are randomly distributed with respect to each other along the backbone.

17. The chelation structure of claim 11, wherein said substance comprises at least one of Fe, Cu, Co, Zn, Mn, U, Hg, and Ga, and wherein the at least one chelator comprises at least one of: 2,3-Dihydroxybenzoic acid; Pyridoxal isonicotinoyl hydrazone (PIH) and derivatives thereof; 2,2'-bipyridyl; 1,2-dimethyl-3-hydroxypyrid-4-one and derivatives thereof; 1-hydroxypyridine 2-one; CP502; ICL670; Dexrazoxane (ADR-925); N,N-bis(2-hydroxybenzyl)ethylenediamine-N,N-diacetic acid (HBED); O-Trensox; and Desferrioxamine (DFO).

18. The chelation structure of claim 1, wherein said substance comprises at least one of Fe and heme, and wherein the at least one chelator comprises Hemopexin.

19. The chelation structure of claim 1, wherein said substance comprises at least one of Fe, Cu, and Mn, and wherein the at least one chelator comprises Penicillamine.

20. The chelation structure of claim 1, wherein said substance comprises:
synthesizing the chelation structure of claim 1.

21. The method of claim 20, wherein said synthesizing the chelation structure comprises:

synthesizing a modified backbone, said modified backbone comprising the backbone, the bonding structures $B_P$ and $B_L$ covalently bonded to the backbone at the corresponding monomeric backbone units, and each polymer structure covalently bonded to the corresponding bonding structure $B_P$; and after said synthesizing, covalently bonding the at least one chelator to the corresponding bonding structures $B_L$ to form the chelation structure.

22. The method of claim 20, wherein said synthesizing the chelation structure comprises: copolymerizing the monomeric backbone units, the at least one polymer structures, and the at least one chelator to form the chelation structure.

23. The method of claim 20, wherein said synthesizing the chelation structure is performed by Radical Addition Fragmentation Transfer (RAFT) Atom Transfer Radical Polymerization (ATRP), or free radical polymerization (FRP).

24. The method of claim 20,
wherein said synthesizing the chelation structure comprises adjusting the chelation structure to control at least one physiological response of a mammal to introduction of the chelation structure into the mammal, wherein said adjusting is selected from the group consisting of adjusting the molecular weight of the backbone, adjusting the total number of polymer structures of the plurality of polymer structures, adjusting the molecular weight of each polymer structure of the plurality of polymer structures, adjusting the shape of each polymer structure of the plurality of polymer structures, and combinations thereof, and wherein the controlled at least one physiological response is at least one of a cell toxicity response, a cell permeability response, a renal clearance time response for removal of the chelation structure from kidneys of the mammal, and a vascular retention time response for retaining the chelation structure in the vascular system of the mammal.

25. A chelation method for reducing an amount of a substance in a mammal, said method comprising:
introducing a chelation structure of claim 1 into the mammal.

26. The method of claim 25, wherein the method further comprises introducing at least one shuttle chelator into the mammal, each shuttle chelator having a log stability constant $K_S$ for binding the substance within an intracellular space of the mammal, said $K_L$ exceeding said $K_S$ for said at least one chelator (L) resulting in said chelation structure pulling the substance from the at least one shuttle chelator within an extracellular space of the mammal.

27. The method of claim 25, wherein the mammal is a human being.

28. The method of claim 25, wherein the mammal is a non-human mammal.

29. The method of claim 25, wherein said substance comprises at least one of Fe, Cu, Co, Zn, Mn, U, Hg, and Ga, and wherein the at least one chelator comprises at least one of: 2,3-Dihydroxybenzoic acid; Pyridoxal isonicotinoyl hydrazone (PIH) and derivatives thereof; 2,2'-bipyridyl; 1,2-dimethyl-3-hydroxypyrid-4-one and derivatives thereof; 1-hydroxypyridine 2-one; CP502; ICL670; Dexrazoxane (ADR-925); N,N-bis(2-hydroxybenzyl)ethylenediamine-N,N-diacetic acid (HBED); O-Trensox; and Desferrioxamine (DFO).

30. The chelation structure of claim 11, wherein said substance consists of said at least one metal.

31. The chelation structure of claim 11, wherein said substance consists of said heme.

32. The chelation structure of claim 1, wherein $R_0$ and $R_1$ are independently selected from the group consisting of an alkene group, an alkyne group, a benzyl group, an aryl group, an acetal group, an aldehyde group, a ketone group, an active sulfone group, a primary amine group, a secondary amine group, a tertiary amine group, a quaternary amine group, a protected amine group, a thiol group, a protected thiol group, a disulfide group, a carboxyl group, a hydroxyl group, a diol group, a protected hydroxyl group, a sulfate group, an amide group, an acrylate group, a methacrylate group, a methacrylamide group, an ester group, and an epoxide group.

33. The chelation structure of claim 1, wherein said substance comprises at least one of Fe, Cu, Co, Zn, Mn, U, Hg, and Ga, and wherein the at least one chelator comprises at least one of: 2,3-Dihydroxybenzoic acid; Pyridoxal isonicotinoyl hydrazone (PIH) and derivatives thereof; 2,2'-bipyridyl; 1,2-dimethyl-3-hydroxypyrid-4-one and derivatives thereof; 1-hydroxypyridine 2-one; CP502; ICL670; Dexrazoxane (ADR-925); N,N-bis(2-hydroxybenzyl)ethylenediamine-N,N-diacetic acid (HBED); O-Trensox; and Desferrioxamine (DFO).

34. Thee chelation structure of claim 1, wherein said substance consists of said at least one metal.

35. The chelation structure of claim 1, wherein said substance consists of said heme.

36. A chelation method for reducing an amount a substance in a mammal, said method comprising:

introducing the chelation structure of claim 11 into the mammal.

37. The method of claim 36, wherein the method further comprises introducing at least one shuttle chelator into the mammal, each shuttle chelator having a log stability constant $K_S$ for binding the substance within an intracellular space of the mammal, said $K_L$ exceeding said $K_S$ for said at least one chelator (L) resulting in said chelation structure pulling the substance front the at least on shuttle chelator within an extracellular space of the mammal.

38. The method of claim 36, wherein the mammal is a human being.

39. The method of claim 36, wherein the mammal is a non-human mammal.

40. The method of claim 36, wherein said substance comprises at least one of Fe, Cu, Co, Zn, Mn, U, Hg, and Ga, and wherein the at least one chelator comprises at least one of: 2,3-Dihydroxybenzoic acid; Pyridoxal isonicotinoyl hydrazone (PIH) and derivatives thereof; 2,2'-bipyridyl; 1,2-dimethyl-3-hydroxypyrid-4-one and derivatives thereof; 1-hydroxypyridine 2-one; CP502; ICL670; Dexrazoxane(ADR-925); N,N-bis(2- hydroxybenzyl)ethylenediamine-N,N-diacetic acid (HBED); O-Trensox; and Desferrioxamine (DFO).

* * * * *